(12) United States Patent
Reineke et al.

(10) Patent No.: US 11,396,571 B2
(45) Date of Patent: Jul. 26, 2022

(54) POLYMERS INCLUDING GALACTOSE BASED BLOCKS AND USES THEREOF

(71) Applicant: REGENTS OF THE UNIVERSITY OF MINNESOTA, Minneapolis, MN (US)

(72) Inventors: Theresa M. Reineke, Vadnais Heights, MN (US); Yogesh Khemchandra Dhande, Minneapolis, MN (US); Bharat Sanjay Wagh, Waialua, HI (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1612 days.

(21) Appl. No.: 15/166,634

(22) Filed: May 27, 2016

(65) Prior Publication Data
US 2016/0346395 A1 Dec. 1, 2016

Related U.S. Application Data

(60) Provisional application No. 62/167,444, filed on May 28, 2015.

(51) Int. Cl.
| | |
|---|---|
| *C12N 15/87* | (2006.01) |
| *C08F 283/06* | (2006.01) |
| *A61K 31/713* | (2006.01) |
| *C08F 283/14* | (2006.01) |
| *A61K 47/54* | (2017.01) |
| *A61K 47/64* | (2017.01) |

(52) U.S. Cl.
CPC .......... *C08F 283/06* (2013.01); *A61K 31/713* (2013.01); *A61K 47/549* (2017.08); *A61K 47/6455* (2017.08); *C08F 283/14* (2013.01); *C12N 15/87* (2013.01)

(58) Field of Classification Search
None
See application file for complete search history.

(56) References Cited

U.S. PATENT DOCUMENTS

2014/0309280 A1* 10/2014 Hudson ................ C12N 15/113
514/44 A

OTHER PUBLICATIONS

Qin, Z. et al., Bioconjugate Chem., 2011, vol. 22: pp. 1503-1512.*
Ahmed, M. et al., Polym. Chem., 2013, vol. 4: pp. 3829-3836.*
Akinc, "Targeted delivery of RNAi therapeutics with endogenous and Exogenous Ligand-Based Mechanisms" 2010 *Molecular Therapy*, 18:1357.
Anderson, "Effects of Trehalose Polycation End-Group Functionalization on Plasmid DNA Uptake and Transfection" 2012 *Biomacromolecules*, 13:2229.
Cheng, "Gene therapy progress and prospects: gene therapy of lysosomal storage disorders" 2003 Gene Ther., 10:1275-1281.
Cheung, "Liver as an ideal target for gene therapy: Expression of CTLA4Ig by retroviral gene transfer" 2002 *Journal of Gastroenterology And Hepatology*, 17:1008.
Dai, "Elucidating the interplay between DNA-condensing and free polycations in gene transfection through a mechanistic study of linear and branched PEI" 2011 *Biomaterials*, 32:8626.
Dash, "Factors affecting blood clearance and in vivo distribution of polyelectrolyte complexes for gene delivery" 1999 Gene therapy, 6:643-50.
De Laporte, "Design of modular non-viral gene therapy vectors" Feb. 2006 *Biomaterials*, 27, 947-54.
Dhande, "NAcetylgalactosamine Block-co-Polycations Form Stable Polyplexes with Plasmids and Promote Liver-Targeted Delivery" Feb. 2016 *Biomacromol.*, 17:830-840.
Dong, "Galactosylated low molecular weight chitosan as a carrier delivering oligonucleotides to Kupffer cells instead of hepatocytes in vivo" 2008 *Journal of Biomedical Materials Research Part A*, 84A:777-84.
Elouahabi, "Formation and Intracellular Trafficking of Lipoplexes and Polyplexes" 2005 *Molecular Therapy*, 11:33647.
European Medicines Agency, (Ed.) "Assessment Report Glybera" 2012.
Fischer, "A novel non-viral vector for DNA delivery based on low molecular weight, branched polyethylenimine: effect of molecular weight on transfection efficiency and cytotoxicity" 1999 *Pharmaceutical Research*, 16:1273-79.
Follenzi, "Targeting lentiviral vector expression to hepatocytes limits transgene-specific immune response and establishes long-term expression of human antihemophilic factor IX in mice" 2003 *Blood*, 103:3700-09.
Gaumet, "Nanoparticles for drug delivery: the need for precision in reporting particle size parameters" May 2008 *European Journal of Pharmaceutics and Biopharmaceutics*, 69:1.
Ginn, "Gene therapy clinical trials worldwide to 2012—an update" 2013 *The Journal of Gene Medicine*, 15:65-77.
Goula, "Polyethylenimine-based intravenous delivery of transgenes to mouse lung" 1998 Gene therapy, 5:1291.
Herweijer, "Gene therapy progress and prospects: hydrodynamic gene delivery" 2007 Gene therapy, 14:99.
Hu, "A Highly Efficient Synthetic Vector: Nonhydrodynamic Delivery of DNA to Hepatocyte Nuclei in Vivo" 2013 ACS Nano, 7:5376-84.
Ishihara, "Accelerated blood clearance phenomenon upon repeated injection of peg-modified pla-nanoparticles" 2009 *Pharmaceutical Research* 2009, 26:2270-79.
Kay, "Viral vectors for gene therapy: the art of turning infectious agents into vehicles of therapeutics" 2001 *Nature medicine*, 7:33-40.
Khorev, "Trivalent, Gal/GalNAc-containing ligands designed for the asialoglycoprotein receptor" 2008 *Bioorganic & medicinal chemistry*, 16:5216-31.
Kim, "Specific Binding of Glucose-derivatized Polymers to the Asialoglycoprotein Receptor of Mouse Primary Hepatocytes" 2001 *Journal of Biological Chemistry*, 276:35312-19.

(Continued)

*Primary Examiner* — Michael D Burkhart
(74) *Attorney, Agent, or Firm* — Mueting Raasch Group

(57) ABSTRACT

Block copolymers that include one or more galactose based blocks and one or more cationic blocks; polyplexes including disclosed block copolymers and one or more nucleic acids; and methods of delivering a nucleic acid to a cell which can include delivering a polyplex to the cell.

17 Claims, 14 Drawing Sheets

(56) References Cited

OTHER PUBLICATIONS

Kwoh, "Stabilization of poly-L-lysine/DNA polyplexes for in vivo gene delivery to the liver" Feb. 1999 *Biochimica et Biophysica Acta (BBA)—Gene Structure and Expression*, 1444:171-90.

Lee, "Affinity enhancement by multivalent lectin-carbohydrate interaction" 2000 *Glycoconjugate journal*, 17:543-551.

Li, "Gene therapy progress and prospects: non-viral gene therapy by systemic delivery" Sep. 2006 *Gene therapy*, 13:1313-9.

Li, "Poly(2-deoxy-2-methacrylamido glucopyranose)- b-Poly(methacrylate amine)s: Optimization of Diblock Glycopolycations for Nucleic Acid Delivery" Feb. 2013 *ACS Macro Letters*, 2:230-5.

Li, "Targeted delivery of macromolecular drugs: asialoglycoprotein receptor (ASGPR) expression by selected hepatoma cell lines used in antiviral drug development" Oct. 2008 *Current drug delivery*, 5:299-302.

Mancheno-Corvo, "Viral gene therapy. Clinical and Translational Oncology" Dec. 2006 *Clinical and Translational Oncology*, 8:858-67.

Mátrai, "Preclinical and clinical progress in hemophilia gene therapy" Sep. 2010 *Current Opinion in Hematology*, 17:387-92.

Moad, "RAFT polymerization and some of its applications" Aug. 2013 *Chem Asian J*, 8:1634-44.

Morille, "Progress in developing cationic vectors for non-viral systemic gene therapy against cancer" Aug.-Sep. 2008 *Biomaterials*, 29(24-25):3477-96.

Ogris, "PEGylated DNA/transferrin-PEI complexes: reduced interaction with blood components, extended circulation in blood and potential for systemic gene delivery" 1999 *Gene therapy*, 6:595-65.

Oupicky, "Importance of lateral and steric stabilization of polyelectrolyte gene delivery vectors for extended systemic circulation" Apr. 2002 *Molecular Therapy*, 5:463-72.

Pack, "Design and development of polymers for gene delivery" Jul. 2005 *Nat Rev Drug Discov*, 4:581-93.

Podetz-Pedersen, "Gene expression in lung and liver after intravenous infusion of polyethylenimine complexes of *Sleeping Beauty* transposons" online Dec. 2009 *Human gene therapy*, 21(2):210-220.

Ponder, "Hemophilia gene therapy: a holy grail found" Mar. 2011 *Molecular Therapy*, 19:427-428.

Prakash, "Targeted delivery of antisense oligonucleotides to hepatocytes using triantennary N-acetyl galactosamine improves potency 10-fold in mice" Jul. 2014 *Nucleic Acids Research*, 42:8796-807.

Pujol, "A Sulfur Tripod Glycoconjugate that Releases a High-Affinity Copper Chelator in Hepatocytes" Jul. 2012 *Angewandte Chemie*, 124:7563-7566.

Rensen, "Design and Synthesis of Novel N-Acetylgalactosamine-Terminated Glycolipids for Targeting of Lipoproteins to the Hepatic Asialoglycoprotein Receptor" 2004 *Journal of Medicinal Chemistry*, 47(23):5798-808.

Rozema, "Dynamic PolyConjugates for targeted in vivo delivery of siRNA to hepatocytes" Aug. 2007 *Proceedings of the National Academy of Sciences*, 104:12982-87.

Ruponen, "Extracellular glycosaminoglycans modify cellular trafficking of lipoplexes and polyplexes" Sep. 2001 A. *Journal of Biological Chemistry*, 276:33875-80.

Sands, "Gene Therapy for Lysosomal Storage Diseases" May 2006 *Mol Ther.*, 13(5):839-849.

Sharma, "Mechanistic studies on aggregation of polyethylenimine-DNA complexes and its prevention" 2005 *Biotechnology and Bioengineering*, 90:614-620.

Shen, "A galactosamine-mediated drug delivery carrier for targeted liver cancer therapy" Oct. 2011 *Pharmacological Research*, 64:410-419.

Sizovs, "Poly(trehalose): Sugar-Coated Nanocomplexes Promote Stabilization and Effective Polyplex-Mediated siRNA Delivery" 2013 *Journal of the American Chemical Society*, 135(41):15417.

Smith, "Diblock Glycopolymers Promote Colloidal Stability of Polyplexes and Effective pDNA and siRNA Delivery under Physiological Salt and Serum Conditions" Jun. 2011 *Biomacromolecules*, 12(8):3015-3022.

Sprouse, "Investigating the Effects of Block versus Statistical Glycopolycations Containing Primary and Tertiary Amines for Plasmid DNA Delivery" 2014 *Biomacromolecules*, 15(7):2616-2628.

Tagami, "Anti-PEG IgM production by siRNA encapsulated in a PEGylated lipid nanocarrier is dependent on the sequence of the siRNA" Apr. 2011 *Journal of Controlled Release*, 151(2):149-154.

Taira, *Non-viral gene therapy: gene design and delivery*. Springer: Tokyo, Japan; 2005. Cover page, title page and table of contents.

Takakura, "Extravasation of macromolecules" Oct. 1998 *Advanced Drug Delivery Reviews*, 34:93-108.

Tang, "Synthesis of a novel tri-antennary galactoside with high hepatocyte targeting" 2007 *Chinese Chemical Letters*, 18:513-515.

Thomas, "Non-viral gene therapy: polycation-mediated DNA delivery" Jul. 2003 *Applied Microbiology and Biotechnology*, 62(1):27-34.

Treat, "Guanidine-Containing Methacrylamide (Co)polymers via aRAFT: Toward a Cell Penetrating Peptide Mimic" 2012 *ACS Macro Letters*, 1(1):100-104.

Van Rossenberg, "Improvement of Hepatocyte-Specific Gene Expression by a Targeted Colchicine Prodrug" Jun. 2003 *ChemBioChem.*, 4:633-639.

Verbaan, "Steric stabilization of poly(2-(dimethylamino)ethyl methacrylate)-based polyplexes mediates prolonged circulation and tumor targeting in mice" Jan. 2004 *The Journal of Gene Medicine*, 6(1):64-75.

Wang, "N-acetylgalactosamine functionalized mixed micellar nanoparticles for targeted delivery of siRNA to liver" 2013 *Journal of Controlled Release*, 166:106-114.

Wu, "Glucose-Containing Diblock Polycations Exhibit Molecular Weight, Charge, and Cell-Type Dependence for pDNA Delivery" 2014 *Biomacromolecules*, 15(5):1716-26.

Xu, "Elucidating the role of free polycationic chains in polycation gene carriers by free chains of polyethylenimine or N,N,N-trimethyl chitosan plus a certain polyplex" Jul. 2014 *International Journal of Nanomedicine*, 9:3231-45.

Xu, "Aqueous RAFT Synthesis of pH-Responsive Triblock Copolymer mPEO—PAPMA—PDPAEMA and Formation of Shell Cross-Linked Micelles" 2008 *Macromolecules*, 41:8429-35.

Young, "Viral gene therapy strategies: from basic science to clinical application" 2006 *The Journal of pathology*, 208(2):299-318.

\* cited by examiner

Scheme 1: Synthesis of methacrylamido N-acetyl-D-galactosamine [a]

[a]Reagents and Conditions: (a) Ac$_2$O, DMAP, Pyridine, 85%. (b) TMSOTf, Ethylene dichloride, 50 °C. (c) N-Hydroxyethyl acrylamide, camphorsulfonic acid, ethylene dichloride, 90 °C, 63% over two steps. (d) NaOMe, pH = 9.0, Methanol, 65%.

Scheme 2: Polymerizatoin of diblock copolymers [b]

[b]Reagents: (a) CPP, V-501, DMSO, 70 °C. (b) V-501, AEMA·HCl, 1M acetate pH = 5.2, 70 °C.

Scheme 3: Synthesis of PEG-based cationic polymer (PEO$_{45}$AEMA$_{32}$) [c]

[c]Reagents: (a) V-501, 2-aminoethylmethacrylamide (AEMA) HCl, 1M acetate buffer pH = 5.2, 70 °C.

POLYMERS INCLUDING GALACTOSE BASED BLOCKS AND USES THEREOF

PRIORITY

This application claims priority to U.S. Provisional Application No. 62/167,444 entitled POLYMERS INCLUDING GALACTOSE BASED BLOCKS AND USES THEREOF, filed May 28, 2015.

GOVERNMENT FUNDING

This invention was made with government support under OD006669 awarded by the National Institutes of Health. The government has certain rights in the invention.

BACKGROUND

The targeted delivery of drugs and nucleic acids to specific tissues has been a long sought after goal and a major hurdle for the field of nanomedicine. Tissue-specific delivery offers advantages of increased therapeutic efficacy, lower toxicity, and reduced immune response. Gene therapies for the treatment of inherited disorders such as hemophilia, and several lysosomal storage diseases (i.e., Hurler syndrome and mucopolysaccharidosis type I) have worked on liver-targeted gene transfer for decades with limited success. The liver has been widely studied for gene delivery applications because of its large size, regenerative ability, and role in the production and secretion of serum proteins. The recent advances in the field of gene therapy such as the clinical approval of Glybera by the European Commission and numerous on-going clinical trials are major advancements that forecast many future ground-breaking genetic therapies. For example, the massive upsurge in the use of genome editing strategies in biomedical research such as CRIPER-Cas9 (clustered regularly interspaced short palindromic repeats with an RNA-guided DNA endonuclease) support the large need for facile synthetic methods for design of targeted vehicles to advance new therapies toward the clinic.

Two classes of nucleic acid delivery vehicles, viral and non-viral vectors, are currently making an important impact in the clinic to advance gene medicines. Indeed, non-viral vectors, such as cationic polymers, have emerged as a valuable class because of their safety, low immunogenicity, and ease of production compared to viruses. Cationic polymers such as polyethylenimine (PEI), poly(L-lysine), and poly(2-aminoethylmethacrylamide) condense plasmid DNA (pDNA) into nanoparticles, termed polyplexes, that are efficiently taken up by cells in vitro through both caveolae and clathrin-mediated endocytic pathways.

However, this in vitro success has yet to be translated into clinical therapies because of several challenges. For example, in the presence of aqueous ions and other charged species, polyplexes formulated with polycationic tend to aggregate (with themselves or other biomolecules such as serum proteins). Such aggregation can severely limit targeting of nanoparticles to specific tissues in vivo, as maintaining a small size has been determined to be one of the most important factors to facilitate tissue specificity. For example, pervious work has shown that polyplexes formed with PEI become trapped in lungs after first-pass circulation due to their large size (indicating rapid aggregation upon in vivo injection). In addition, PEI polyplexes also suffer from rapid clearance from the blood by the reticuloendothelial system (RES) due to non-specific charge-mediated interactions with serum proteins. To prevent these detrimental interactions, polyethylene glycol (PEG) is commonly used as a hydrophilic outer layer to sterically-stabilize polyplexes to prevent aggregation and prolong circulation times by reducing non-specific interactions with the RES. However, PEG has a limited effect on polyplex stability and has been shown to undergo accelerated blood clearance after multiple polyplex injections. To this end, new structures and assemblies of polymeric vehicles are needed to overcome these challenges and facilitate clinical advancement of new gene-based therapeutics.

SUMMARY

Disclosed are block copolymers that include one or more galactose based blocks; and one or more cationic blocks.

Also disclosed are polyplexes that include a block copolymer that includes one or more galactose based blocks; and one or more cationic blocks; and one or more nucleic acids.

Also disclosed are methods of delivering a nucleic acid to a cell, the methods include delivering a polyplex to a cell, the polyplex including a block copolymer that includes one or more galactose based blocks; and one or more cationic blocks; and one or more nucleic acids.

BRIEF DESCRIPTION OF THE FIGURES

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
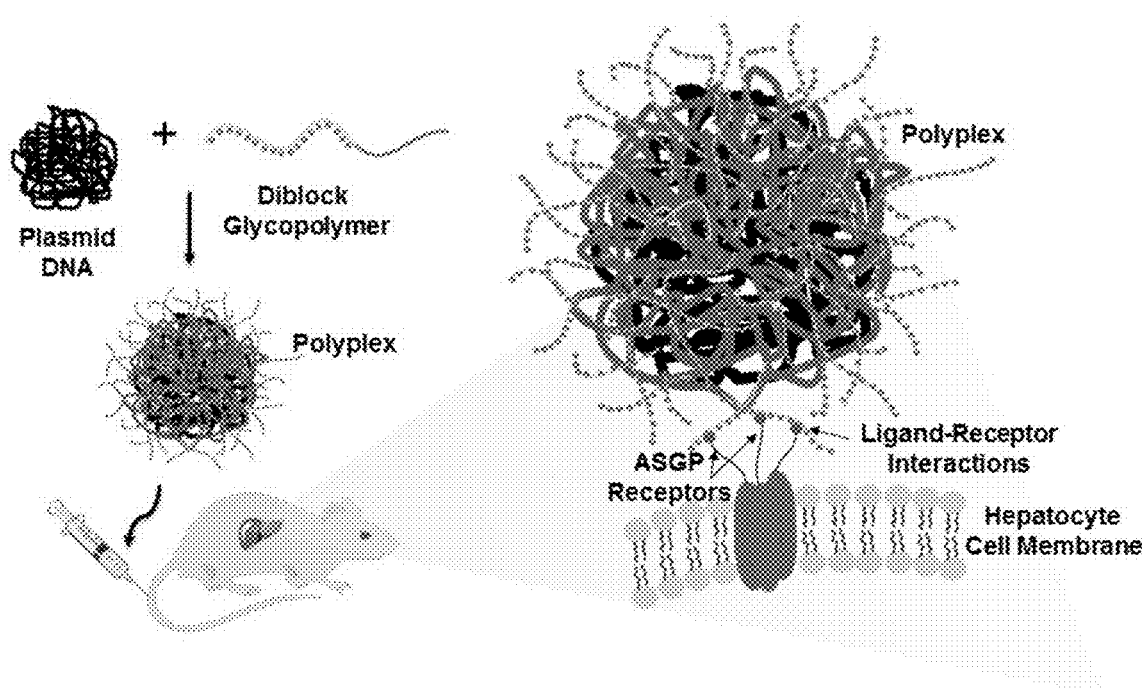
FIG. 1 shows an illustrative schematic of polyplex formation and interactions of presented N-acetyl-D-galactosamine (GNA or GalNAc) ligands with ASGP receptors on hepatocytes (not drawn to scale).

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

"Include," "including," or like terms means encompassing but not limited to, that is, including and not exclusive.

Disclosed herein are block copolymers that include one or more galactose based blocks, and one or more cationic blocks. The galactose based blocks and the cationic blocks generally include polymerized residues of a plurality of galactose monomer units and cationic monomer units respectively. The block copolymer can be formed using various methods, including Reversible Addition-Fragmentation Chain Transfer (RAFT) methods. Block copolymers so formed can be utilized in various different therapeutic methods, including for example liver-targeted delivery of therapeutic agents.

In some embodiments, the galactose based monomers or blocks can include materials derived from N-acetyl-D-galactosamine (GNA). In some illustrative embodiments, materials based on or derived from GNA may be useful for targeting liver cells because GNA and galactose are known to be useful in targeting asialoglycoprotein (ASGP) receptor lectins on liver hepatocytes. A specific illustrative embodiment of a galactose based monomer or block can include methacrylamido N-acetyl-D-galactosamine (which can be referred to as "MAGalNAc").

In some embodiments, the cationic block can include a discernable block within the copolymer that presents a net positive charge. Alternatively, the cationic block can be described as being derived from cationic monomers. Illustrative cationic monomers can include, for example acrylamide based monomers or more specifically methacrylamide monomers such as aminoethylmethacrylamide (AEMA), 3-guanidinopropyl methacrylamide (GPMA), or combinations thereof. GPMA can be synthesized, for example as found in Treat, N.J., et al. *ACS Macro Lett.* 2012, 1(1), 100-104, the disclosure of which is incorporated herein by reference thereto.

In some embodiments, the galactose based blocks and the cationic blocks can independently be of a fixed specific length or a variable length. In some embodiments, the galactose based blocks can be of a specific, fixed length and the cationic blocks can be of a variable length. In some embodiments, the block copolymer can include not less than 10 repeating units of the cationic block, not less than 14 repeating units of the cationic block, not less than 30 repeating units of the cationic block, or at least 80 repeating units of the cationic block. In some embodiments, the block copolymer can include not less than 30 repeating units of the galactose based block, not less than 40 repeating units of the galactose based block, or not less than 60 repeating units of the galactose based block.

Specific illustrative examples of disclosed block copolymers can include poly methacrylamido N-acetyl-D-galactosamine-block-aminoethylmethacrylamide (pMAGalNAc-b-AEMA) and poly methacrylamido N-acetyl-D-galactosamine-block-3-guanidinopropyl methacrylamide (pMAGalNAc-b-GPMA). The names of the block copolymers can provide an indication of the length of the blocks, for example a block copolymer having a 41 unit block of poly methacrylamido N-acetyl-D-galactosamine-block-aminoethylmethacrylamide (pMAGalNAc) and a 14 unit block of 3-guanidinopropyl methacrylamide (pMAGalNAc-b-GPMA) can be represented as $pMAGalNAc_{41}$-b-$GPMA_{14}$.

Disclosed block copolymers can be formed using various methods, including Reversible Addition-Fragmentation Chain Transfer (RAFT) methods. In some RAFT methods, a chain transfer agent such as 4-cyano-4-(propylsufanylthiocarbonyl) sulfanylpentanoic acid (CPP) and a free radical initiator such as 4,4'-azobis(4-cyanopentanoic acid) which can also be referred to as V-501 (commercially available from Sigma-Aldrich) can be utilized. CPP can be synthesized, for example as disclosed in Xu, X., et al. *Macromolecules* 2008, 41 (22), 8429-8435.

Also disclosed are polyplexes including disclosed block copolymers and one or more nucleic acids. The term "nucleic acid" as used herein refers to nucleic acid molecules including DNA (gDNA, cDNA), oligonucleotides (double or single stranded), R A (sense RNAs, antisense RNAs, mRNAs, tRNAs, rRNAs, small interfering RNAs (siRNAs), double-stranded RNAs (dsRNA), short hairpin RNAs (shRNAs), piwi-interacting RNAs (PiRNA), micro RNAs (miRNAs), small nucleolar RNAs-(SnoRNAs), small nuclear RNAs (SnRNAs)), ribozymes, aptamers, DNAzymes, ribonuclease-type complexes and other such molecules as herein described. The term "nucleic acid" includes non-naturally occurring modified forms, as well as naturally occurring forms. The term "nucleic acid" also includes other families of compounds such as oligonucleotide analogs, chimeric, hybrid and mimetic forms.

Also disclosed are methods of delivering a nucleic acid to a cell which can include delivering a polyplex to the cell.

The present disclosure is illustrated by the following examples. It is to be understood that the particular examples, assumptions, modeling, and procedures are to be interpreted broadly in accordance with the scope and spirit of the disclosure as set forth herein.

Disclosed herein are hydrophilic structures, in some embodiments highly hydrophilic structures, including sugars. Such structures could serve a dual purpose: to maintain colloidal stability of polyplexes and serve as ligands to cell surface lectins promoting tissue-specific delivery. To this end, a series of cationic diblock glycopolymers derived from or including N-acetyl-D-galactosamine (GNA or GalNAc) were created as targeted delivery systems to the asialoglycoprotein (ASGP) receptor lectins on liver hepatocytes. It is thought, but not relied upon that incorporation of ligands in a block copolymer could provide multivalent interactions of nanosystems with cell surface lectins. Multiple ligands from the same chain or different chains on the same polyplex may interact with the receptors to achieve relatively high binding affinity.

FIG. 1 shows an illustrative schematic of polyplex formation and interactions of presented GNA ligands with ASGP receptors on hepatocytes (not drawn to scale). Many GNA-block polycations complex with polyanionic pDNA in the polyplex core to form nanoparticles that display neutral GNA sugar blocks near the polyplex surface which promote ASGP lectin binding and cell-specific polyplex internalization. FIG. 1 illustrates possible vehicle design parameters to promote core-shell polyplex formation with pDNA with exposed GNA blocks forming the polyplex shell to promote binding interactions to the carbohydrate recognition domains (CRDs) of ASGP receptors. Complexation of the cationic blocks of many polymer chains with anionic pDNA facilitates polyplex formation, which is entropically driven by the release of counterions into solution. Herein, we show that this design motif promotes colloidal stable polyplex formation that promotes significantly higher specificity in pDNA delivery both in vitro and in vivo as compared to control polymers consisting of PEG and poly(glucose) shell blocks. The presence of polymerized GNA ligands resulted in cell type-dependent delivery, with higher protein expression in ASGP receptor-presenting HepG2 cells as compared to HeLa cells, which lack these receptors. In vivo distribution experiments in mice may reveal a higher amount of pDNA and Cy7-labeled polymer in the liver as compared to lungs and other organs. Disclosed herein therefore are polymerized form of GNA ligands that promote targeted delivery to liver hepatocytes and offer a facile design motif for promoting liver-specific therapeutic delivery.

The present disclosure is illustrated by the following examples. It is to be understood that the particular examples, assumptions, modeling, and procedures are to be interpreted broadly in accordance with the scope and spirit of the disclosure as set forth herein.

EXAMPLES

Materials

All the reagents for polymer synthesis were purchased from Aldrich (Milwaukee, Wis.) at the highest available purity available and used as received unless mentioned otherwise. AEMA monomer was purchased from Polysciences (Warrington, Pa.) and used directly. The chain transfer agent (CTA) 4-cyano-4-(propylsulfanylthiocarbonyl)sulfanylpentanoic acid (CPP) was synthesized as previously reported (Smith, A. E.; Sizovs, A.; Grandinetti, G.; Xue, L.; Reineke, T. M. Biomacromolecules 2011, 12, 3015; and Xu, X.; Smith, A. E.; Kirkland, S. E.; McCormick, C. L. Macromolecules 2008, 41, 8429). 4,4'-Azobis(4-cyanopentanoic acid) (V-501) was recrystallized twice from methanol prior to use.

All types of cell culture media used in this study were purchased from Life Technologies (Grand Island, N.Y.): Dulbecco's Modified Eagle Medium (DMEM, high glucose, Glutamax™ supplement), Reduced-Serum Medium (OptiMEM®, Glutamax™ supplement), Heat Inactivated Fetal Bovine Serum (HI FBS), Phosphate Buffered Saline (PBS) pH=7.4, and Antibiotic-Antimycotic (100×). MTT (3-(4,5-Dimethylthiazol-2-yl)-2,5-Diphenyltetrazolium Bromide) for cell viability assays was purchased from Invitrogen. Human hepatocellular carcinoma (HepG2), and human cervical carcinoma (HeLa) cell lines were purchased from ATCC (Manassas, Va.).

gWiz-luc plasmid DNA, used for the luciferase assay, was purchased from Aldevron (Fargo, N. Dak.). All other in vitro experiments were performed with pCMV-lacZ (also purchased from Aldevron). Commercially available transfection reagents were used as positive controls in this study: Glycofect (a donation from Techulon, Inc., Blacksburg, Va.) and JetPEI (purchased from Polyplus-transfection Inc., Illkirch, France), were used as standards and positive controls for transfections. Unless specified otherwise, all biological experiments were performed in triplicate, and the mean and standard deviation of these data are reported in all figures and tables.

Example 1: Synthesis of MAGalNAc Monomer

Figure 2:
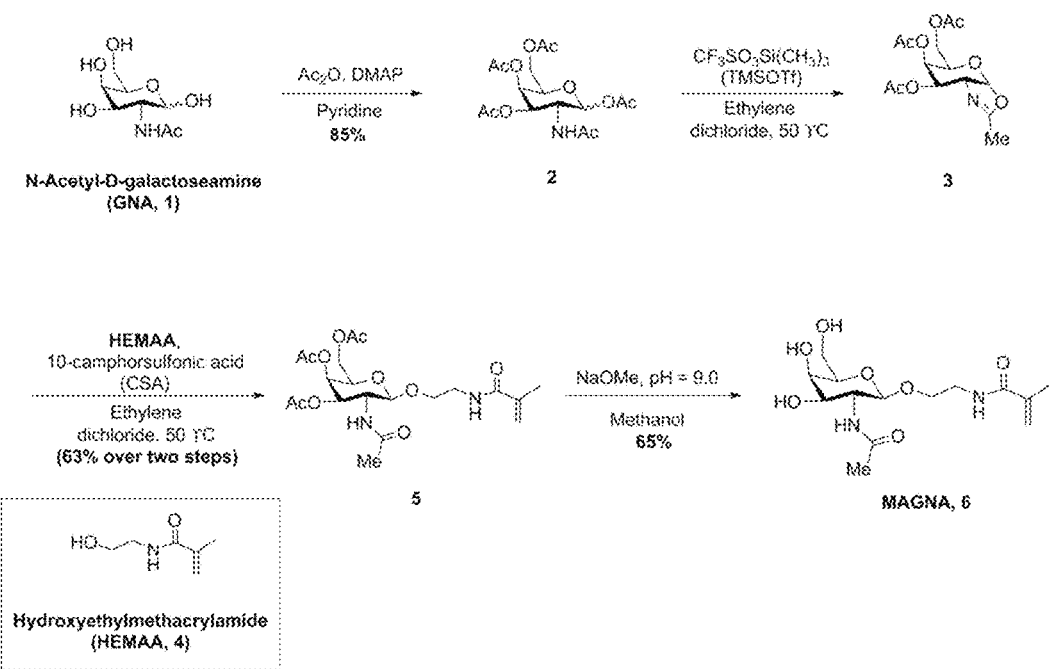
FIG. 2 is a scheme for the synthesis of methacrylamido N-acetyl-D-galactosamine (MAGalNAc).

The GNA-derived monomer, methacrylamido N-acetyl-D-galactosamine (MAGalNAc, 6), was synthesized in 4 facile steps as shown in the scheme in FIG. 2. The hydroxyls of N-acetyl-D-galactosamine (GNA, 1) were first acetylated to create O-acetylated GNA (2). The acetylated product 2 was then treated with trimehtylsilyltrifluoromethanesufonate (TMSOTf) in dichloroethane at 50° C. to yield 1,2-oxazoline (3). The oxazoline was ring-opened with hydroxyethylmethacrylamide (4) to synthesize O-acetylated MAGalNAc (5). Lastly, the 0-acetyl groups of 5 cleaved methanolysis at pH=9 to yield the final methacrylamidomonomer structure, MAGalNAc (6)

A more specific illustrative synthesis of the methacrylamido N-Acetyl-D-Galactosamine Monomer (MAGalNAc) can include the following steps.

Synthesis of Acetylated GNA (2)

To a solution of GNA (1) (5.15 g, 23.9 mmol) in dry pyridine (240 mL) at room temperature was added ester acetic anhydride (20.0 g, 196 mmol), DMAP (0.028 g, 0.238 mmol), and stirred for 12 hours. After 12 hours, the reaction mixture was diluted with ethyl acetate (240 mL), and washed with 1N HCl solution (3×100 ml). The organic layer was then washed with sat. $NaHCO_3$ (1×100 ml), distilled water (1×100 ml), brine (1×100 ml), dried with $Na_2SO_4$, and filtered. The solvent was concentrated under reduced pressure and dried under high vacuum to afford 7.2 g (18.8 mmol, 78% yield) of acetylated GNA (2) as white foam. IR (film) 3286, 1741, 1677, 1657, 1558, 1540, 1369, 1321, 1211, 1108, 1009, 937; $^1$H NMR (300 MHz) δ 6.21 (d, J=6.0 Hz, 1H), 5.43 (m, 2H), 5.22 (dd, J=15.0, 3 Hz, 1H), 4.73 (m, 1H), 4.24 (m, 1H), 4.1 (m, 2H), 2.17 (bs, 6H), 2.03 (bs, 6H), 1.95 (s, 3H); $^{13}$C NMR (125 MHz) δ 171.09, 170.39, 170.35, 170.22, 168.91, 91.24, 68.49, 67.74, 66.68, 61.29, 46.94, 23.07, 20.94, 20.73, 20.64, 20.62. FIRMS (ESI) calculated for $C_{16}H_{23}NO_{10}$+Na=412.1220. found 412.1214.

Synthesis of (3aR,5R,6R,7R,7aR)-5-(acetoxymethyl)-2-methyl-3a,6,7,7a-tetrahydro-5H-pyrano[3,2-d]oxazole-6,7-diyl diacetate (referred to herein as oxazoline), 3)

To a solution of 2 (4.87 g, 12.5 mmol) in 1,2-dichloroethane (130 ml) under a nitrogen atmosphere was added TMSOTf (3.06 g, 13.8 mmol), and the solution was heated to 50° C. and stirred for 12 hours. After, it was cooled down to room temperature, triethylamine was added to neutralize the solution. Post neutralization, the solution was concentrated under reduced pressure and the crude mixture was dried under vacuum. The product was purified via column chromatography by eluting the product in a 20:1 $CHCl_3$/MeOH mobile phase. Semi-pure oxazoline (3, 4 g) was isolated from the column, and taken directly to the next step.

Synthesis of Acetylated MAGalNAc (5)

To a solution of 3 (4 g) in 1,2-dichloroethane (72 ml) under a nitrogen atmosphere was added 2-hydroxyethylmethacrylamide (4, 5.55 g, 43 mmol), and camphor sulfonic acid (CSA, 0.333 g, 1.43 mmol) and refluxed for 12 hours. After, the solution was cooled to room temperature and neutralized with triethylamine. The crude was then concentrated under reduced pressure and dried under high vacuum. The product was then purified via column chromatography where it was eluted with a 20:1 $CHCl_3$/MeOH mobile phase. IR (film) 3293, 3078, 2935, 1744, 1658, 1619, 1533, 1433, 1369, 1304, 1221, 1166, 1135, 1074, 1044, 929, 733, 589 $cm^{-1}$; $^1H$ NMR (500 MHz) δ 6.44 (m, 1H), 5.89 (m, 1H), 5.76 (s, 1H), 5.35 (s, 1H), 5.35 (m, 1H), 5.11 (dd, J=15, 5 Hz, 1H), 4.62 (d, J=5 Hz, 1H), 4.14 (m, 3H), 3.91 (m, 2H), 3.71 (m, 2H), 3.39 (m, 1H), 2.15 (s, 3H), 2.05-1.94 (m, 12H); $^{13}C$ NMR (125 MHz) δ 171.11, 170.65, 170.46, 170.21, 168.81, 139.65, 120.2, 100.97, 70.83, 70.30, 68.04, 66.57, 61.48, 51.05, 39.12, 23.26, 20.70 (3C), 18.65. HRMS (ESI) calculated for $C_{20}H_{30}N_2O_{10}$+Na=481.1798. found 481.1806.

Synthesis of MAGalNAc (6)

To a solution of 5 (3.6 g, 8.10 mmol) in MeOH (300 ml), sodium methoxide (2.72 g, 33.2 mmol) was added to obtain a solution pH of ~9. The reaction was stirred for 12 hours and then the solution was neutralized with Dowex 50 W×2 hydrogen form resin. The resin was filtered and the solution was concentrated under reduced pressure and dried under vacuum. The product was then re-dissolved in water and lyophilized to dryness. No further purification was required. IR (film) 3306, 2926, 1651, 1613, 1529, 1433, 1372, 1310, 1206, 1156, 1115, 1051, 930, 584 $cm^{-1}$; $^1H$ NMR (500 MHz) δ 5.62 (s, 1H), 5.38 (s, 1H), 4.36 (d, J=10 Hz, 1H), 3.9-3.5 (m, 8H), 3.45-3.27 (m, 2H), 1.9 (s, 3H), 1.84 (s, 3H); $^{13}C$ NMR (125 MHz) δ 174.66, 171.80, 138.89, 121.23, 101.48, 75.05, 70.96, 67.85, 67.72, 60.93, 52.34, 39.36, 22.15, 17.61. HRMS (ESI) calculated for $C_{14}H_{24}N_2O_7$+Na=355.1481. found 355.1484.

Example 2: Synthesis and Characterization of MAGalNAc Polymers

To design targeted delivery vehicles that retain colloidally stability, two methacrylamide-based monomers (one cationic and the other galactose based) were selected for controlled polymerization by the Reversible Addition-Fragmentation Chain Transfer (RAFT) mechanism to yield well-defined diblock copolymers. Two examples are included herein, with the first including 2-aminoethylmethacrylamide (AEMA) as the cationic block and the second including 3-guanidinopropyl methacrylamide (GPMA) as the second. Both were combined with a monomer based on GNA, in order to impart ASGP receptor targeting along with hydrophilic/steric stabilization properties.

A trithiocarbonate based chain transfer agent (CTA), 4-cyano-4-(propylsulfanylthiocarbonyl) sulfanylpentanoic acid (CPP) was used to achieve control over radical polymerization of these monomers to create the block copolymer structures. The initial RAFT studies on MAGalNAc (6) were performed on a 100 mg-200 mg scale, which lead to approximately 60% conversion in 6 hours with excellent polydispersity indices (<1.1). To yield a large batch of polymer to carry through for numerous analytical and biological characterization, 1 g of MAGalNAc (6) was polymerized in the presence of CPP and the free radical initiator V-501 in a 4:1 $H_2O$/MeOH mixture at 70° C. for 6 hours.

Figure 3:
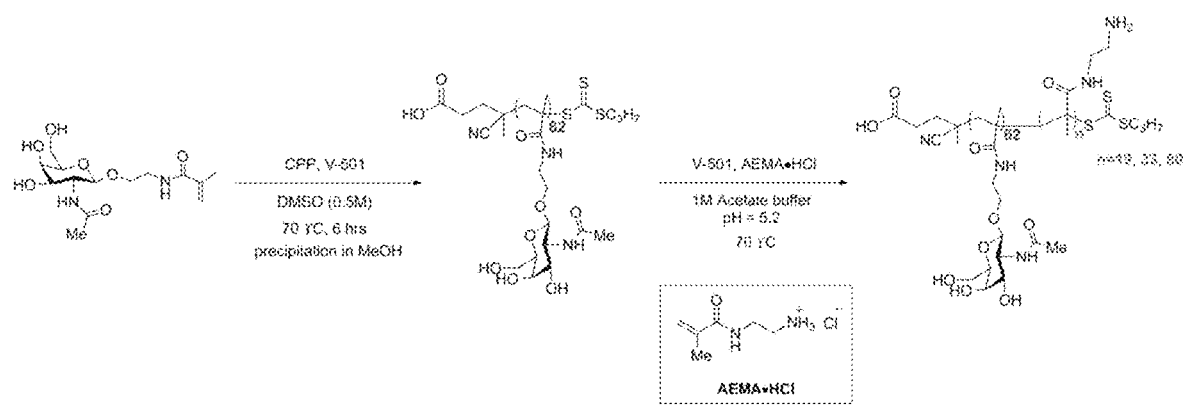
FIG. 3 is a scheme for the polymerization of poly(methacrylamido N-acetyl-D-galactosamine) (MAGalNAc).

As shown in Scheme 2 in FIG. 3, the macroCTA poly (methacrylamido N-acetyl-D-galactosamine) or MAGalNAc$_{62}$ was constructed in high yield (92%) and lowdispersity of 1.17 at this large scale. This macroCTA was isolated by dialysis against water using a 3.5 KDa M.W.C.O. dialysis bag; an alternative way is precipitation in cold methanol. The MAGalNAc$_{62}$ macroCTA was subsequently chain-extended with AEMA to produce three diblock polymers with AEMA repeat units of 19, 33, and 80 (Table 1). AEMA polymerizations were performed in a 0.5 M aqueous acetate buffer (pH=5.2) to minimize hydrolysis and maintain the trithiocarbonate chain end groups.

Specific illustrative synthesis of MAGalNAc polymers can include the following.

Synthesis of pMAGalNAc$_{62}$-b-pAEMA$_x$ by RAFT Polymerization

A solution of CPP (0.009 g, 0.032 mmol), MAGalNAc (0.765 g, 2.3 mmol), and V-501 (8.8×10$^{-4}$ g, 0.0032 mmol) in 4.6 ml of 4:1 $H_2O$/ethanol was added to a 25 mL round bottom flask equipped with a magnetic stir bar. The stirred solution was then purged with nitrogen for 30 min, and the flask was placed in a preheated oil bath at 70° C. The reaction was terminated after 3 hours by quenching the reaction tube in liquid nitrogen, followed by exposure to air. After purification by dialysis against water (pH 4 to 5) and lyophilization, the MAGalNAc$_{62}$ macroCTA was chain extended with AEMA to yield three diblock polymers following a similar procedure as previously published (Wu, Y.; Wang, M.; Sprouse, D.; Smith, A. E.; Reineke, T. M. Biomacromolecules 2014, 15, 1716). In general, AEMA (0.132 g, 0.799 mmol), MAGalNAc$_{62}$ (0.1 g), and V-501 (2.6×10$^{-4}$ g, 9.4×10$^{-4}$ mmol) were dissolved in 7.9 ml of 0.5 M acetate buffer (pH 5.2) and added to a 25 ml round bottom flask equipped with a magnetic stir bar. After purging with nitrogen for 30 min, the stirred reaction was allowed to proceed at 70° C. for 7.5 h. The reaction mixture was then quenched by cooling the reaction vessel in liquid nitrogen and exposure to air. The product was purified by dialysis against DI water (pH 4 to 5) and lyophilized to dryness.

pMAGalNAc$_{41}$-b-pGPMA$_{14}$ and pMAGalNAc$_{41}$-b-pGPMA$_{36}$ were synthesized using a procedure similar to that above.

Size exclusion chromatography (SEC) was used to determine the molecular weight (number average, $M_n$ and weight averaged, $M_w$) and dispersity (Đ) for the above prepared polymers using an aqueous eluent of 1.0 wt % acetic acid/0.1 M $Na_2SO_4$. A flow rate of 0.3 mL/min, Eprogen (Downers Grove, Ill.) columns [CATSEC1000 (7 μm, 50×4.6), CATSEC100 (5 μm, 250×4.6), CATSEC300 (5 μm, 250×4.6), and CATSEC1000 (7 μm, 250×4.6)], a Wyatt HELEOS II light scattering detector (λ=662 nm), and an Optilab rEX refractometer (λ=658 nm) were used. Astra V (version 5.3.4.18, Wyatt Technologies, Santa Barbara, Calif.) was utilized for the determination of $M_n$, Đ, and do/dc of the (co)polymers. $^1H$ NMR measurements were performed with a temperature-controlled Varian 400-MR (Palo Alto, Calif.) spectrometer operating at a frequency of 399.7 MHz. Samples were prepared in $D_2O$ (HOD internal standard), and spectra were recorded for each copolymer at a temperature of 70° C. Block copolymer compositions were determined by comparing resonances of the MAGalNAc block with those associated with the AEMA or GPMA blocks. The results are presented in Table 1 below.

Example 3: Synthesis of PEG-Based Block Polycation Control

Figure 4:
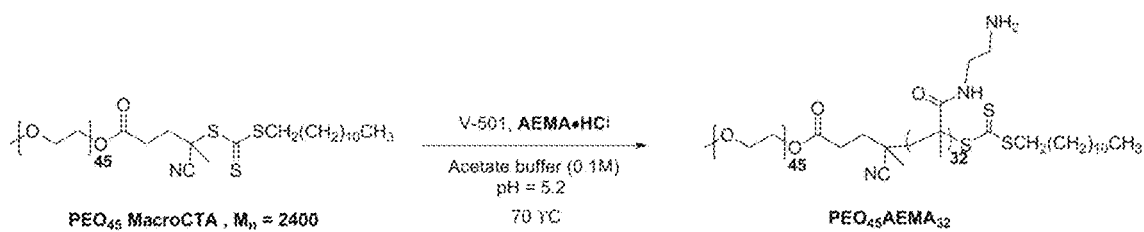
FIG. 4 is a scheme for the preparation of PEG-based block polycation with AEMA.

As a control, a PEG-based block polycation was also prepared by extending a PEO macroCTA ($M_n$=2400, 45 repeats of ethylene oxide) with AEMA (Scheme 3 in FIG. 4) to create $PEO_{45}$-b-$AEMA_{32}$. An additional control was created according to previously published procedures that contained a polymerized methacrylamido-glucose (MAG) and chain extended with AEMA to create P($MAG_{46}$-b-$AEMA_{13}$). This control was created to examine the specificity of the sugar block for hepatocyte delivery.

Figure 5:
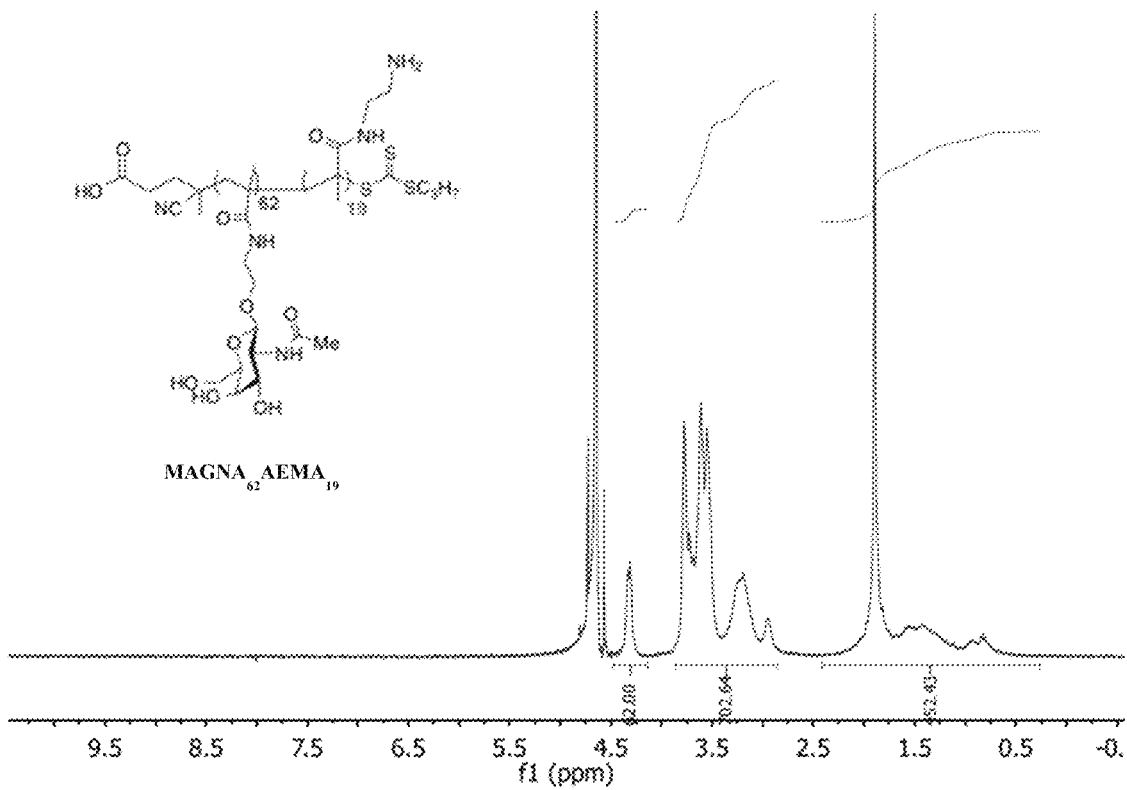
FIG. 5 is a $^1H$ NMR spectrum of $MAGalNAc_{62}AEMA_{19}$.
Figure 6:
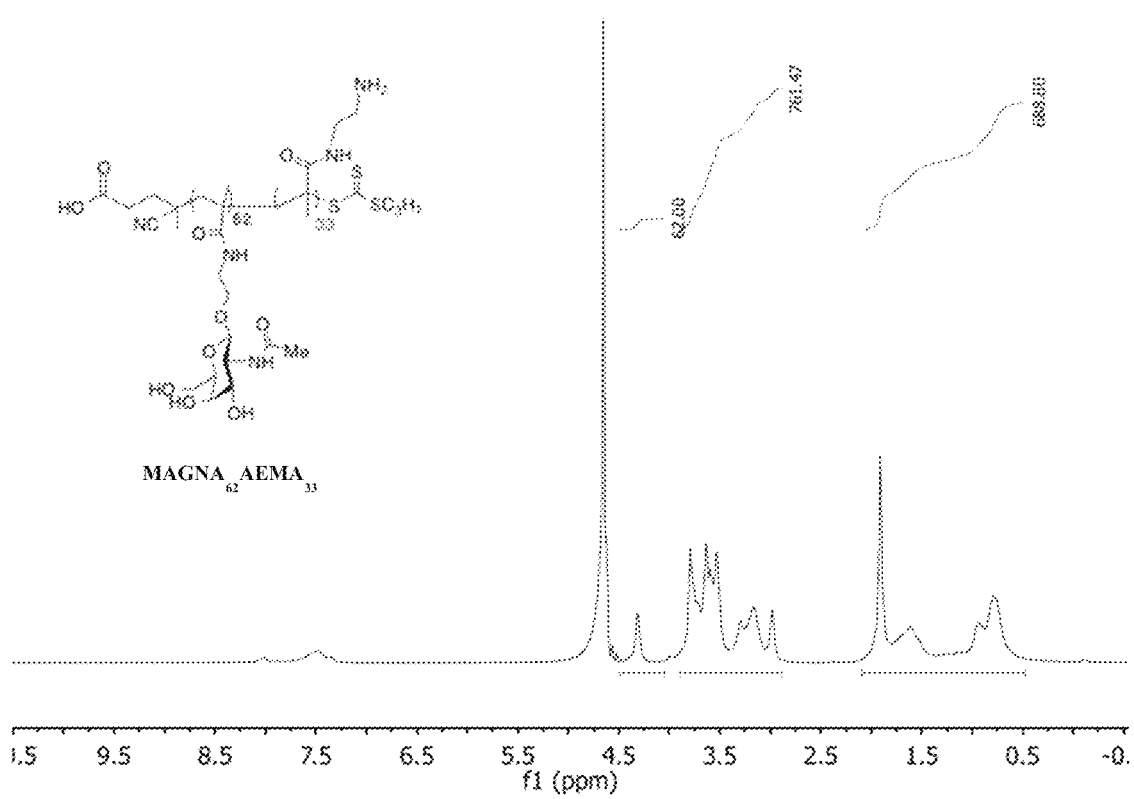
FIG. 6 shows a $^1H$ NMR spectrum of $MAGalNAc_{62}AEMA_{33}$.
Figure 7:
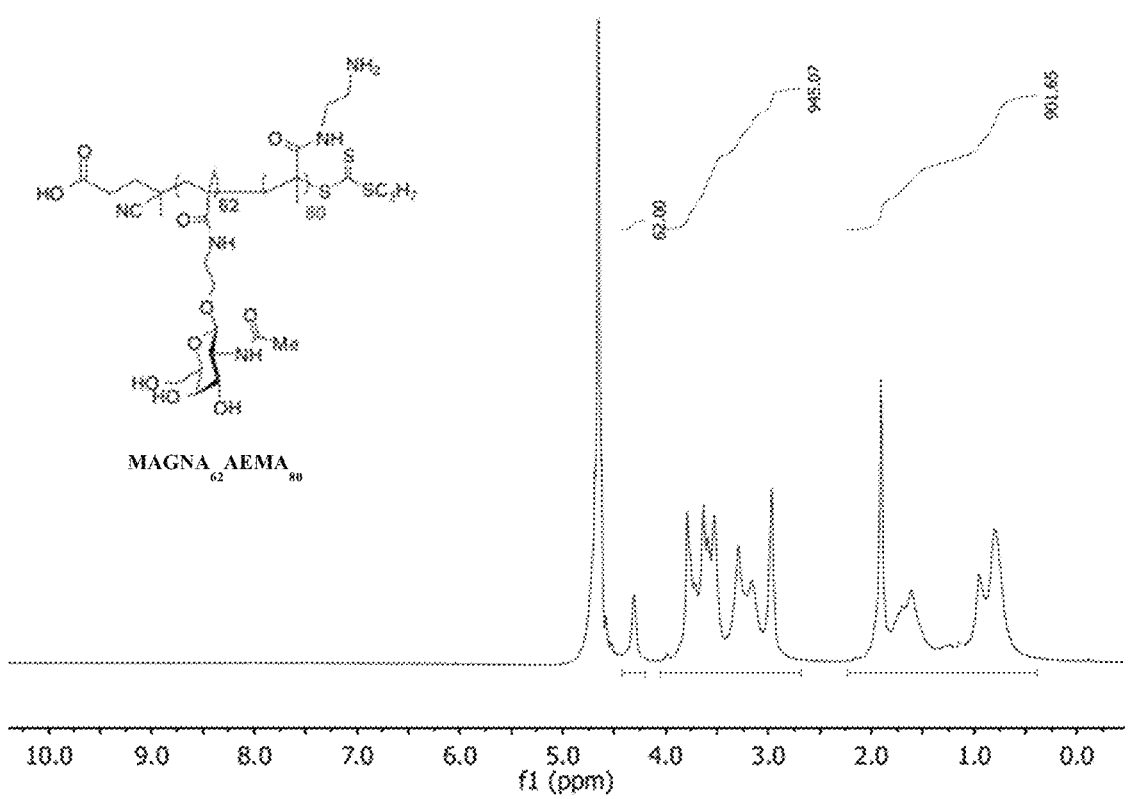
FIG. 7 shows a $^1H$ NMR spectrum of $MAGalNAc_{62}AEMA_{80}$.
Figure 8:
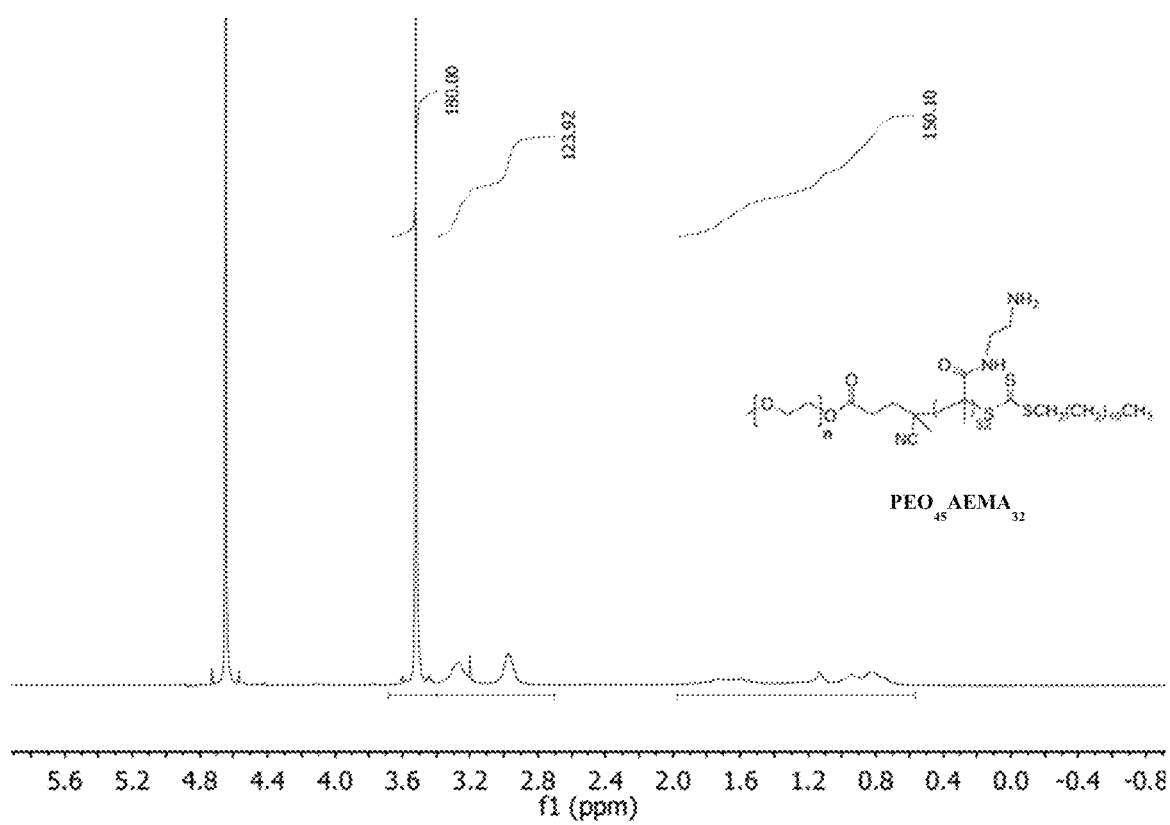
FIG. 8 shows a $^1H$ NMR spectrum of $PEO_{62}AEMA_{32}$.
Figure 9:
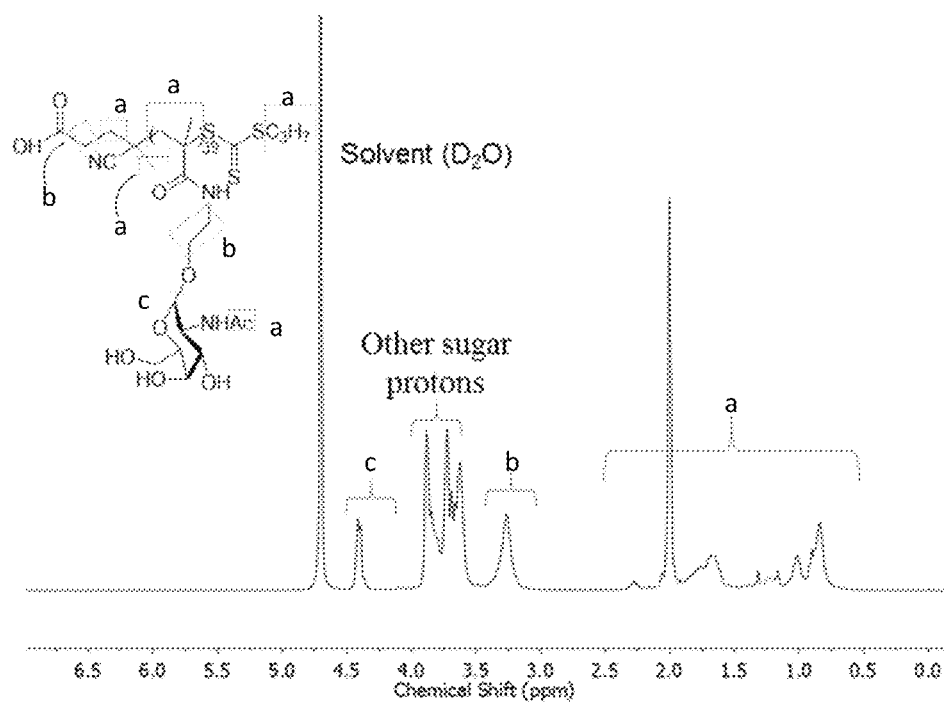
FIG. 9 is a $^1H$ NMR of $pMAGalNAc_{41}$ in $D_2O$.
Figure 10:
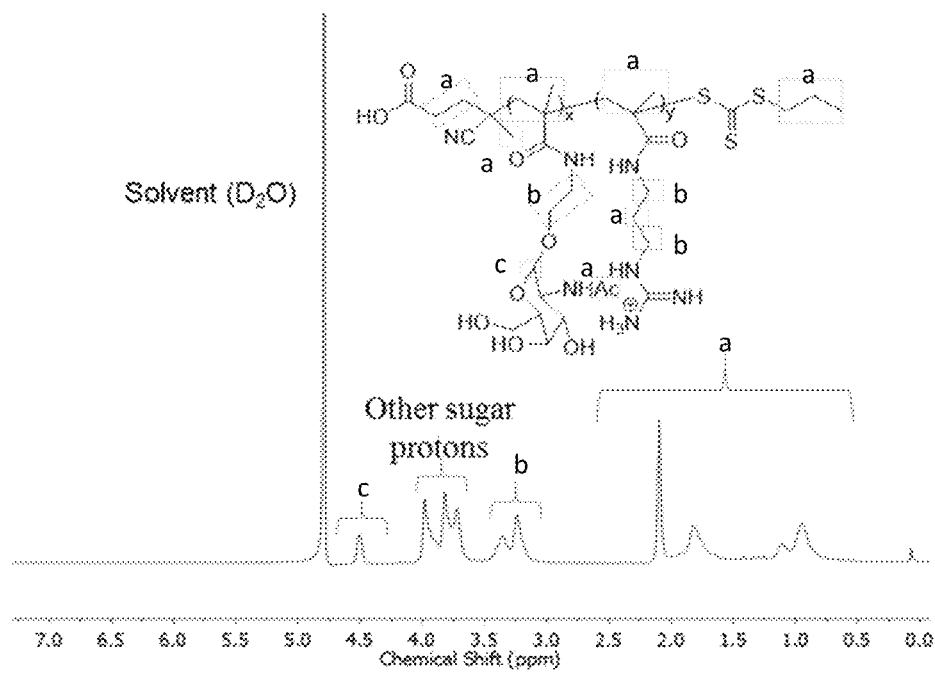
FIG. 10 is a $^1H$ NMR of $pMAGalNAc_{41}$-b-$GPMA_{14}$ in $D_2O$.

The MAGalNAc and PEG block polycations were analyzed with $^1H$ NMR. FIG. 5 shows a $^1H$ NMR spectrum of $MAGalNAc_{62}AEMA_{19}$. FIG. 6 shows a $^1H$ NMR spectrum of $MAGalNAc_{62}AEMA_{33}$. FIG. 7 shows a $^1H$ NMR spectrum of $MAGalNAc_{62}AEMA_{80}$. FIG. 8 shows a $^1H$ NMR spectrum of $PEO_{62}AEMA_{32}$. FIG. 9 shows the $^1H$ NMR of $pMAGalNAc_{41}$ in $D_2O$. FIG. 10 shows the $^1H$ NMR of $pMAGalNAc_{41}$-b-$GPMA_{14}$ in $D_2O$.

Analysis of the MAGalNAc, and PEG block polycations via $^1H$ NMR revealed degree of polymerizations in agreement with those calculated from the size exclusion chromatography (SEC) measurements (Table 1 below). SEC chromatograms of $MAGalNAc_{62}$ and the diblock polymers were unimodal with moderate dispersity indices (Đ<1.35) indicating fairly controlled polymerizations. The moderate dispersities of diblock polymers may be attributed to the high percent conversion (92%) for the AEMA chain extension.

TABLE 1

Molecular Weight, Dispersity, and Degree of Polymerization (DP) of Polymers Synthesized in This Study

| Polymer | $M_n$ (KDa) [a] | Đ [a] | MAGalNAc DP [a, b] | AEMA DP [a, b] |
|---|---|---|---|---|
| $pMAGalNAc_{62}$ | 20 | 1.17 | 62 | N/A |
| $pMAGalNAc_{62}$-b-$pAEMA_{19}$ | 23 | 1.29 | 62 | 19 |
| $pMAGalNAc_{62}$-b-$pAEMA_{33}$ | 25 | 1.32 | 62 | 33 |
| $pMAGalNAc_{62}$-b-$pAEMA_{80}$ | 31 | 1.32 | 62 | 80 |
| $PEO_{45}$-b-$pAEMA_{32}$ | 6.5 | 1.11 | N/A | 32 |
| $pMAGalNAc_{20}$ | 6.92 | 1.03 | 20 | — |
| $pMAGalNAc_{41}$ | 14.1 | 1.03 | 41 | — |
| $pMAGalNAc_{41}$-b-$pGPMA_{14}$ | 17.3 | 1.08 | 41 | 14 |
| $pGPMA_{53}$ | 12.0 | 1.02 | — | 53 |
| $pGPMA_{34}$ | 7.88 | 1.06 | — | 34 |
| $pMAGalNAc_{41}$-b-$pAEMA_{36}$ | 20.0 | 1.15 | 41 | 36 |
| $pAEMA_{48}$ | 8.26 | 1.14 | — | 48 |

[a] As determined by SEC using an aqueous eluent of 0.1M $Na_2SO_4$ in 1.0 wt % acetic acid at a flow rate of 0.3 mL/min on Eprogen columns [CATSEC1000 (7 μm, 50 × 4.6), CATSEC100 (5 μm, 250 × 4.6), CATSEC300 (5 μm, 250 × 4.6), and CATSEC1000 (7 μm, 250 × 4.6)] with a Wyatt HELEOS II static light scattering detector (λ = 662 nm), and an Optilab rEX refractometer (λ = 658 nm).
[b] The degree of polymerizations were confirmed by $^1H$ NMR on a temperature-controlled Varian 400-MR spectrometer operating at a frequency of 399.7 MHz.

Polyplex Formulation and Size Measurements

To examine the interactions of plasmid DNA (pDNA) with each of the block copolycations, polymer solutions were added to pDNA solutions (50 ng/μL), vortexed, and allowed to sit at room temperature for 1 hour.

A specific illustrative method of forming the polyplex formulations includes the following. Stock solutions of polymer were prepared in water at a concentration of 15 mM of ionizable amines. The stock solutions were diluted in water to appropriate concentrations necessary for desired N/P ratios. Polyplexes were formulated by adding equal volume of polymer solution to pDNA in water. For DNA binding studies by electrophoresis, aqueous polymers solutions (10 μL) at appropriate concentrations were added to 10 μL pDNA solution (50 ng/μL) to make polyplexes at various N/P values. For example, to achieve an N/P=5, the stock polymer solution was diluted to 0.75 mM of ionizable amines before adding 10 μL of it to pDNA solution at 50 ng/μL (0.15 mM phosphates). Polyplex formulations were kept at room temperature to equilibrate for one hour before running them on 0.6% agarose gel containing 0.3 μg/mL ethidium bromide. Gel electrophoresis was carried out at 80 V for 45 minutes. The binding of pDNA to cationic polymers resulted in its retardation on the gel which was visualized and imaged (Supporting Information, Figure S10) with a Fotodyne FOTO/Analyst™ Luminary/FX workstation.

Figure 11:
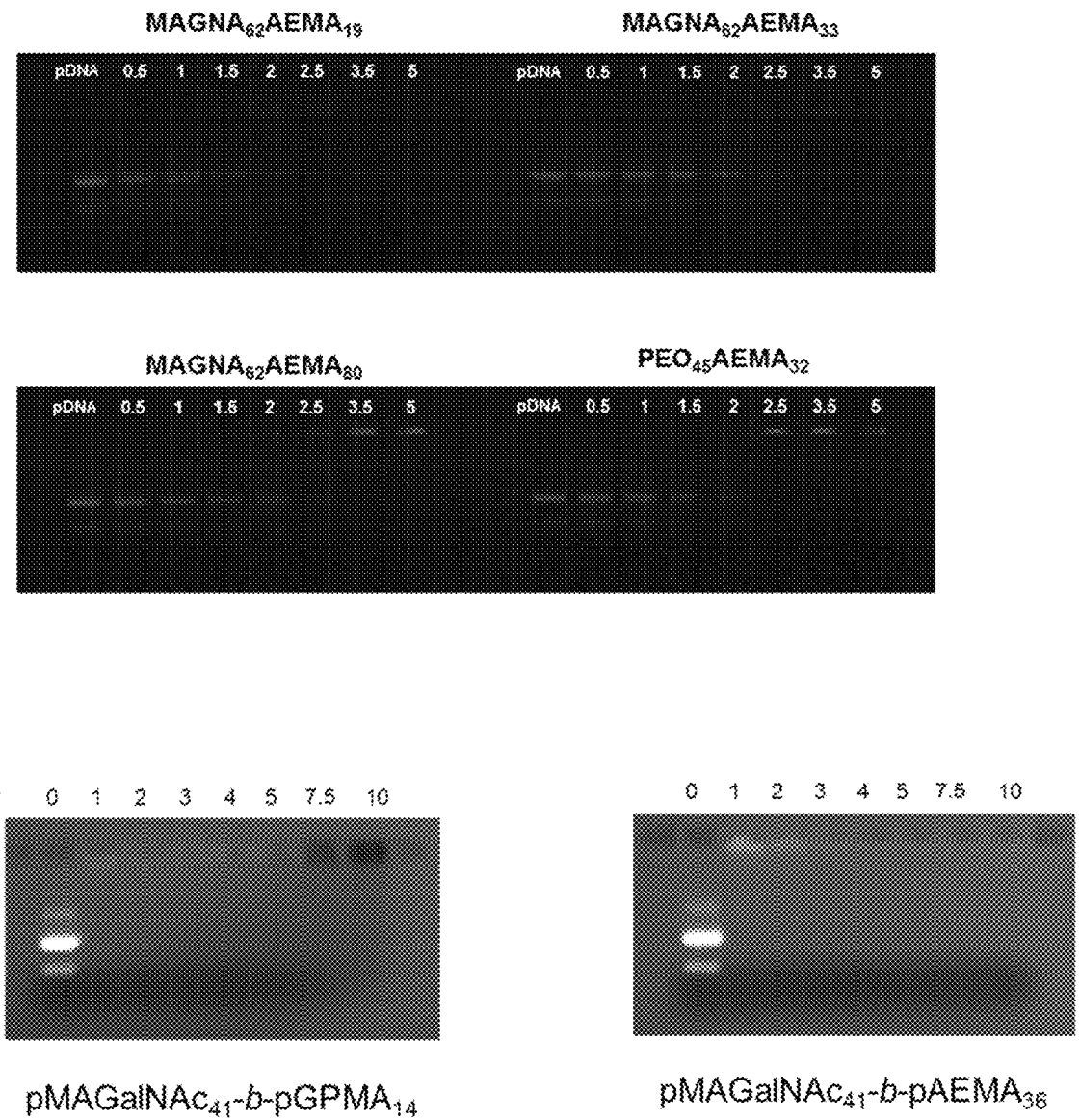
FIG. 11 shows gel electrophoresis of pDNA and polyplexes.

The N/P ratio of each polyplex formulation was calculated as the molar ratio of ionizable amines on the polymer ("cationic block") to phosphates on pDNA. It should be noted that in the polymerized form, the $pK_a$ of the amine group on AEMA is 8.5. As a result, most of the amines are in the protonated form when the polyplexes are formulated in water. Polyplex formation is signified as a shift or lack of pDNA migration in the agarose gel (see FIG. 11, which shows gel electrophoresis of pDNA and polyplexes. The numbers marking each lane indicate the N/P ratio). $MAGalNAc_{62}AEMA_{19}$ and $PEO_{45}AEMA_{32}$ completely retarded the migration of pDNA at N/P values of 2.5 and above. $MAGalNAc_{62}AEMA_{33}$ and $MAGalNAc_{62}AEMA_{80}$ achieved the same effect at N/P values of 3.5 and higher. Results are also shown for $MAGalNAc_{41}$-b-$pGPMA_{14}$ and $MAGalNAc_{41}$-b-$pGPMA_{36}$. Based on these results, N/P values of 2.5, 5 and 7.5 were selected to evaluate polyplex stability and cytotoxicity.

A specific illustrative method for measuring the sizes of the particles and their Zeta potentials can include the following. The particle size and zeta potential measurements were carried out by dynamic light scattering using Zetasizer Nano-ZS from Malvern Instruments Ltd. For particle size measurements, polyplexes were prepared by adding 25 μL of aqueous polymer solutions to 25 μL pDNA (20 ng/μL in water). The polymer concentrations were adjusted to achieve N/P ratios of 2.5, 5, and 7.5 as described earlier. The mixture was incubated for an hour before adding 100 μL of OptiMEM. The sample was analyzed immediately to determine the particle size at 0 h. Additional measurements were performed after 2 and 4 hours to study the stability of polyplexes over time. Z-average diameters calculated by the instrument at 0, 2 and 4 h time points are reported. For zeta potential measurements, 150 μL of aqueous polymer solution was added to 150 μL pDNA (20 ng/μL in water) to achieve N/P values of 2.5 and 5. After incubation at room temperature for an hour, 600 μL water was added to each sample. The zeta potential was measured by using a detection angle of 17°.

Figure 12:
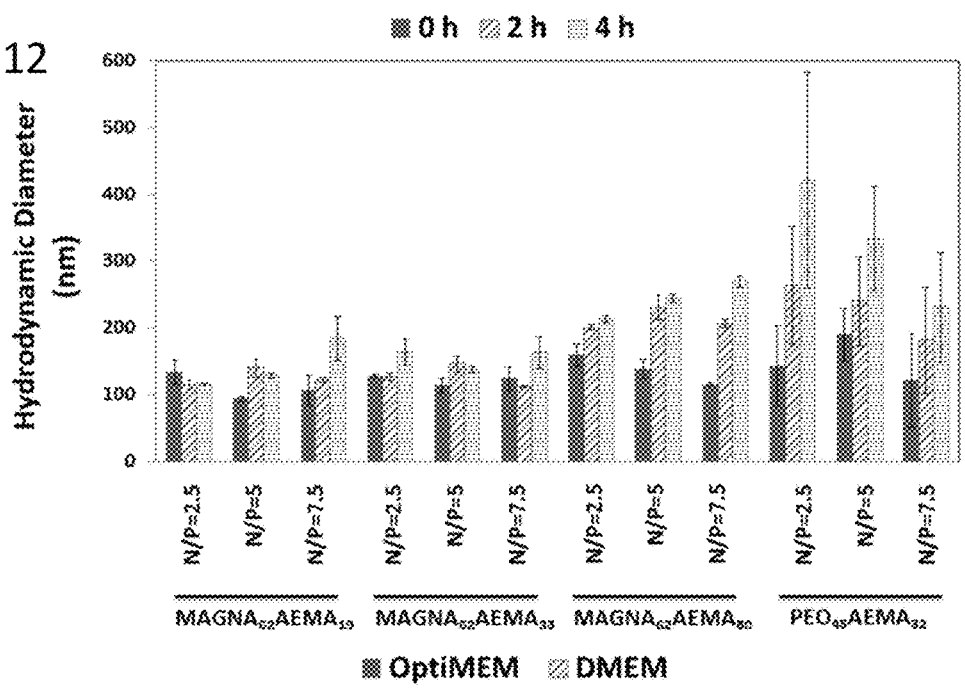
FIG. 12 shows size measurements of polyplexes determined by dynamic light scattering.

Polyplex sizes can be seen in FIG. 12. FIG. 12 shows size measurements of polyplexes determined by dynamic light scattering as discussed above. Polyplexes were formed by mixing equal volumes of pDNA and polymer solutions at N/P values of 2.5, 5, and 7.5. The mixtures were incubated at room temperature for 1 h before adding twice the volume of reduced-serum OptiMEM. The time of OptiMEM addition is indicated as 0 h, with additional measurements reported at 2 h and 4 h as mean±standard deviation (n=3 experiments).

The MAGalNAc polyplexes were formulated in water at N/P ratios of 2.5, 5, and 7.5. At these N/P ratios, the particle diameters were found to range from 90 to 160 nm in size (average diameter) immediately after the addition of reduced-serum OptiMEM. The polyplexes formed with $MAGalNAc_{62}AEMA_{19}$ and $MAGalNAc_{62}AEMA_{33}$ were found to be more colloidally stable in reduced-serum OptiMEM compared to $PEO_{45}AEMA_{32}$ polyplexes. After four hours at room temperature, $MAGalNAc_{62}AEMA_{19}$ and $MAGalNAc_{62}AEMA_{33}$ polyplexes increased in diameter by less than 50% at N/P ratios of 2.5 and 5. In contrast, $PEO_{45}AEMA_{32}$ polyplexes exhibited an increase of 200% and 75% during the same time period at N/P ratios 2.5 and 5 respectively. This is likely due the low molecular weight of PEG block which is less bulky and therefore less efficient at providing steric stabilization. In addition, $MAGalNAc_{62}AEMA_{80}$ polyplexes were found to aggregate to a higher extent than polyplexes formed with shorter cationic blocks. This difference is likely due to the fact that the polyplex formulations with the longer cationic blocks contain fewer polymer chains (and thus fewer hydrophilic sugar blocks) at the same N/P values than those with shorter cationic blocks. Fewer MAGalNAc blocks coating the polyplexes likely leads to a reduction in steric hindrance, and thus less protection from aggregation. This feature highlights the role of the neutral/hydrophilic sugar block in promoting polyplex colloidal stability.

Figure 13:
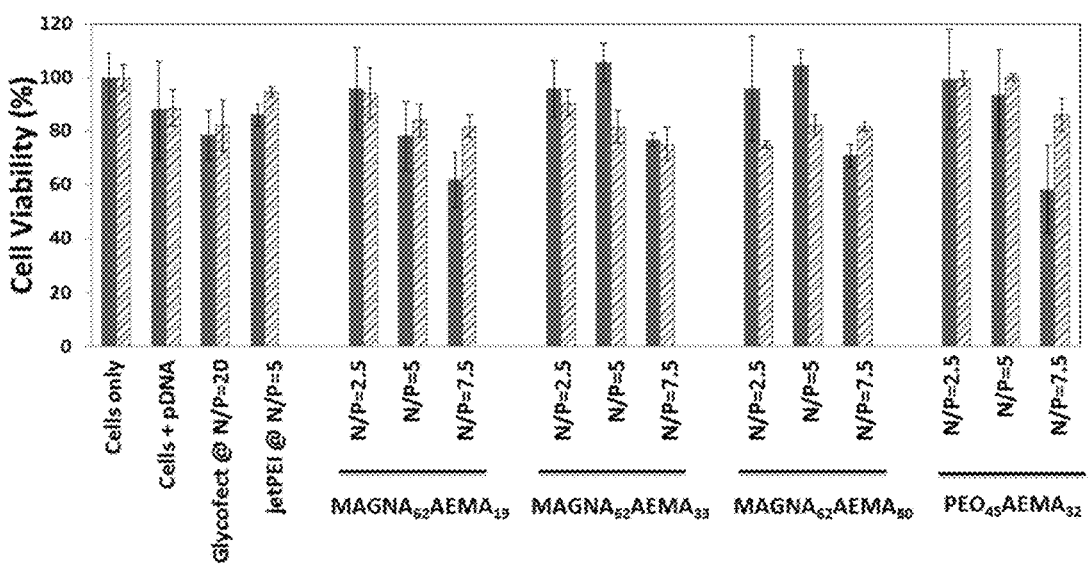
FIG. 13 shows cell viabilities assessed using MTT assays.

Viabilities of cells treated with the polyplex formulations were assessed using MTT assays. FIG. 13 shows HepG2 cell viabilities as measured by MTT assay. MTT assays were carried out by plating HepG2 or HeLa cells at a density of 50,000 cells/well in a 24-well plate. Polyplexes were prepared an hour before transfection by adding 175 μL of aqueous polymer solutions at appropriate concentrations to 175 μL of pDNA (20 ng/μL in water) to achieve desired N/P values (2.5, 5, and 7.5) as described earlier. The polymer-pDNA mixtures were vortexed and kept at room temperature for an hour before using them for transfections. Transfections were carried out 24 hours after plating. DMEM was aspirated off from each well and cells were washed with 1×PBS. Polyplexes were diluted two times with either reduced-serum OptiMEM or DMEM containing 10% FBS. The diluted solution (300 μL) was then added to each well. Four hours after transfection, 1 mL of DMEM containing 10% FBS was added to each well. At 24 hours post-transfection, media was replaced with DMEM containing 10% FBS and 0.5 mg/mL MTT. Cells were incubated at 37° C. and 5% $CO_2$ for an hour, after which the media were aspirated from each well. The cells were then washed once with 1×PBS and 600 μL DMSO was added to each well to lyse the cells. The plates were placed on an orbital shaker for 15 minutes to allow complete lysis. An aliquot (200 μL) was removed from each well and transferred to a clear 96-well plate. Absorbance was measured at 570 nm using a TECAN GENios Pro microplate reader from Tecan (Männedorf, Switzerland). Data were normalized such that the negative control (cells that were not transfected) had a cell viability of 100%.

Cells were transfected with polyplexes formed at N/P of 2.5, 5, and 7.5 in either OptiMEM (blue solid fill) or DMEM containing 10% FBS (red diagonal fill). 24 h after transfection, cells were incubated with DMEM containing 10% FBS and 0.5 mg/mL MTT for 15 minutes, washed and lysed by addition of DMSO. The data were normalized to indicate 100% cell viability for the un-transfected control (cells only). Values are reported as mean±standard deviation (n=3 experiments).

Assays were performed in both reduced-serum OptiMEM and DMEM containing 10% fetal bovine serum (FBS). In general, cell viability decreased at higher N/P values (FIG. 13). At an N/P of 7.5, all polyplex formulations revealed some toxicity. No clear difference in cell viability was observed between OptiMEM and DMEM containing 10% FBS with the exception of $PEO_{45}AEMA_{32}$ and $MAGalNAc_{62}AEMA_{19}$, polyplex formulations, which showed higher cytotoxicity in OptiMEM. At N/P values of 2.5 and 5, the MAGalNAc and PEG-based block polymers showed similar or higher cell viabilities compared with control polymers (Glycofect and jetPEI). Thus, the subsequent cellular uptake and gene expression studies were carried out for polyplexes formulated at these lower N/P values.

Cellular Uptake of Cy5-Labeled Polyplexes

Cells were cultured in DMEM containing 10% FBS in 75 $cm^2$ flasks at 37° C. under 5% $CO_2$-atmosphere to maintain physiological pH. The culture media were supplemented with Antibiotic-Antimycotic solution from Life Technologies at the final concentration of 10 μg/mL penicillin, 10 μg/mL streptomycin and 25 ng/mL Fungizone®. Cells were monitored for confluency regularly and passaged as necessary. For plating, cells were trypsinized and suspended in DMEM containing 10% FBS. A hemocytometer was used to count cells prior to plating. Trypan blue was used to distinguish between viable and dead cells. For luciferase assay, 50,000 cells were plated per well in 24-well plates. For flow cytometry experiments, 100,000 cells were plated per well in 12-well plates.

Polyplex uptake was studied by flow cytometry with HepG2 (carry ASGP receptors) and HeLa (lack ASGP receptors) cells using Cy5-labeled pDNA (Cy5-pDNA) for polyplex formulation. Glycofect, JetPEI, and $MAG_{46}AEMA_{13}$ (a glucose-derived non-targeted polymer) were examined and compared as control polyplex formulations. Propidium iodide (PI), a double stranded DNA stain that only permeates compromised cell membranes, was used to assay dead cell fraction.

Cy5-labeled pDNA was prepared using a Label IT® kit from Mirus Bio LLC (Madison, Wis.) following and completed according to the manufacturer's protocol. Polyplexes were prepared as described earlier using the Cy5-labeled pDNA. Twenty four hours prior to transfection, cells were seeded at a density of 100,000 cells/well in 12-well plates.

Polyplexes were prepared by addition of 350 µL of aqueous polymer solutions to 350 µL of Cy5-labeled pDNA (20 ng/µL in water) an hour before transfection. DMEM was aspirated off from each well and cells were washed with 1×PBS. Polyplexes were diluted with 1400 µL of OptiMEM, and 600 µL of this mixture was added to each well for transfection. Four hours later, transfection media was collected into falcon tubes. Cells were detached from the plate by adding 0.5 mL of Trypsin-EDTA (0.05%). DMEM containing 10% FBS (1 mL) was then added to each well and cells were transferred to the same falcon tubes used to collect transfection media. Cells were then washed once with 1×PBS and resuspended in 100 µL PBS containing 40 µg/mL propidium iodide. Flow cytometry experiments were performed on a BD FACSVerse from BD Biosciences (San Jose, Calif.) and analyzed using FlowJo software.

Figures 14A, 14B:
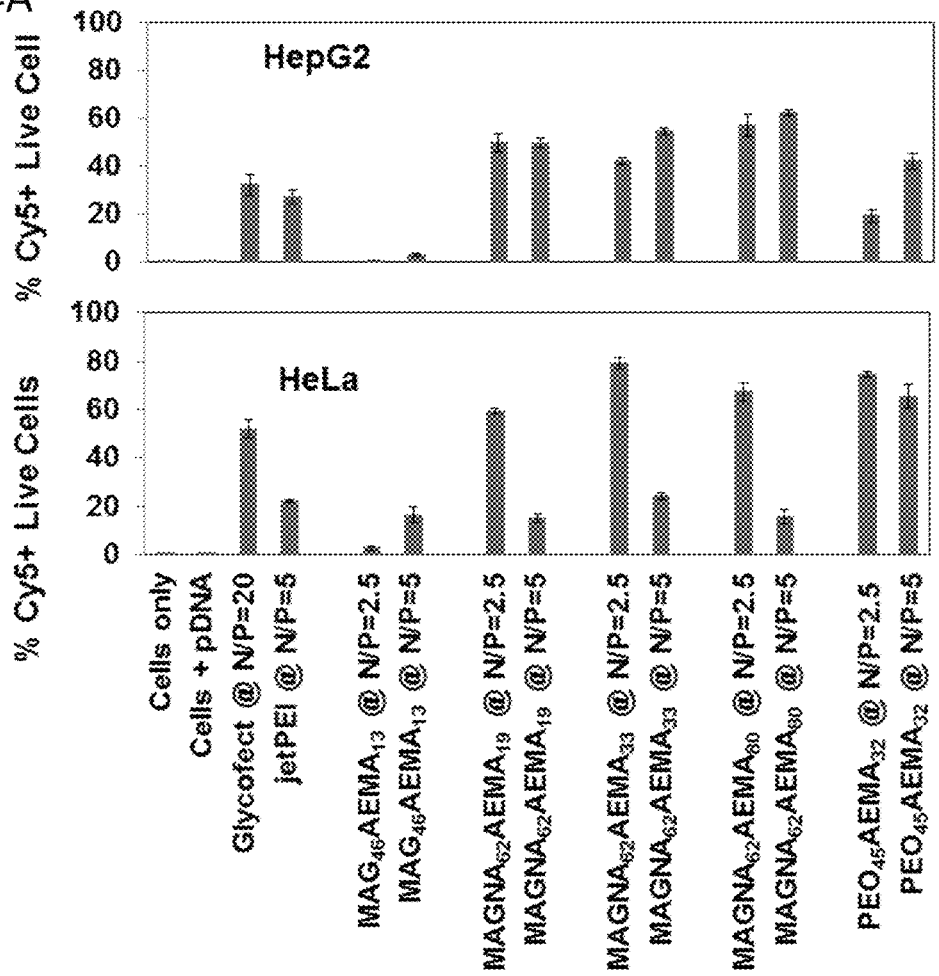
FIGS. 14A and 14B show uptake of Cy5-labeled pDNA in HepG2 and HeLa cells as a percentage Cy5-positive live HepG2 cells (FIG. 14A) and a percentage Cy5-positive live HeLa cells (FIG. 14B).
Figure 15A:
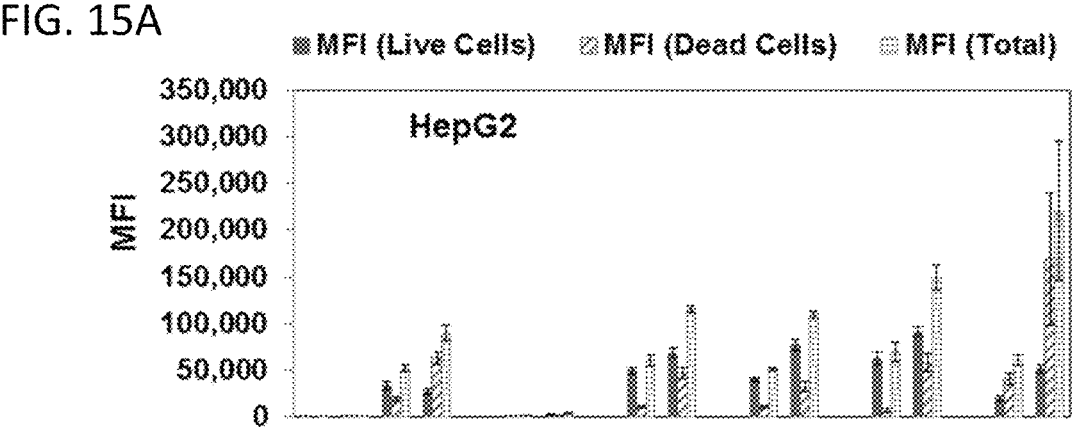
FIGS. 15A and 15B show uptake of Cy5-labeled pDNA in HepG2 and HeLa cells. (A) Mean fluorescence index (MFI=% Cy5-positive cells times the mean Cy5 intensity) values of live HepG2 cells (blue, solid fill), dead HepG2 cells (red, diagonal fill), and all HepG2 cells (green, horizontal fill) (FIG. 15A); and mean fluorescence index values of live (blue, solid fill), dead (red, diagonal fill), and all HeLa cells (green, horizontal fill) (FIG. 15B).
Figure 15B:
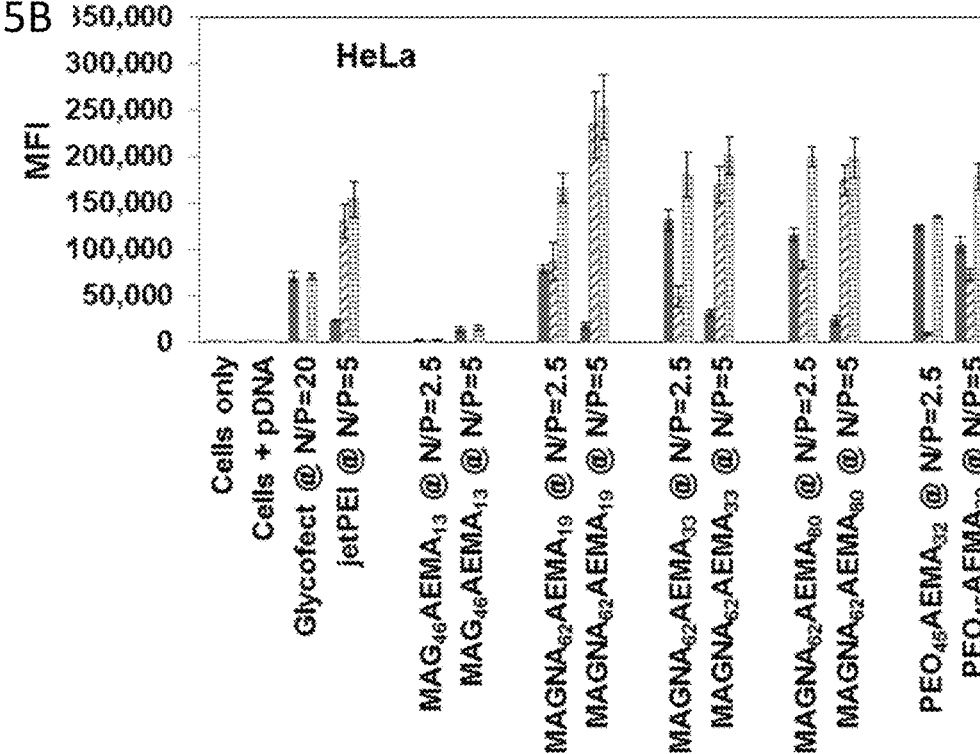

FIGS. 14A and 14B and 15A and 15B show the percentage of Cy5-positive live cells, and mean fluorescence index (MFI), respectively. MFI is calculated by multiplying the percent of Cy5-positive cells by the mean fluorescence intensity. As shown in FIG. 14A, HepG2 cells show higher uptake of Cy5-pDNA formulated with the MAGalNAc block polymers than Cy5-pDNA formulated with jetPEI, $MAG_{46}AEMA_{13}$, or $PEO_{45}AEMA_{32}$ polymers. Cellular uptake was found to be dependent on the N/P ratios. Higher N/P ratios allowed for a greater uptake of Cy5-pDNA in HepG2 cells as indicated by the increased MFI value (FIG. 15A). HeLa cells, on the other hand, generally showed a lower percentage of Cy5-positive live cells (FIG. 14B) and MFI values (FIG. 15B) at N/P of 5 than at N/P of 2.5. This opposite trend was the result of the higher cytotoxicity of the MAGalNAc polymers to HeLa than HepG2 cells as indicated by PI staining. When both PI-negative and positive HeLa cells were included in the analysis, MFI values were higher at N/P of 5 than at 2.5, indicating that polyplex uptake is associated with cytotoxicity (FIG. 15B). A similar effect was observed previously in uptake studies with glucose-derived block polycations, where a high fraction of Cy5-positive cells were also found to be PI-positive at the higher N/P ratio.[44] $PEO_{45}AEMA_{32}$ also shows lower polyplex internalization at N/P of 5 than at 2.5 (FIGS. 14B and 15B). The difference in MFI between N/P of 2.5 and 5 for $PEO_{45}AEMA_{32}$ was smaller than that for MAGalNAc polymers. This fact is consistent with the lower toxicity of $PEO_{45}AEMA_{32}$ as indicated by lower percent PI-positive HeLa cells compared to MAGalNAc polymers. $MAG_{46}AEMA_{13}$, which has negligible toxicity at both the N/P values, shows higher MFI values (p<0.01) and percentage of Cy5-positive cells (p<0.01) at the higher N/P value but overall the delivery efficiency of this polymer was much lower in both cell types compared to the MAGalNAc block polymers at the low N/P ratios studied. Glycofect showed a higher percentage of Cy5-positive cells (p<0.01) and MFI (p<0.01) in HeLa compared to HepG2 cells. In comparison, jetPEI showed similar levels of MFI (p>0.05) and percent Cy5-positive (p>0.05) cells in both cell lines.

Transgene Expression

For the luciferase gene expression assay, HepG2 or HeLa cells were transfected in 24-well plates at a density of 50,000 cells/well. Polyplexes were prepared an hour before transfection by adding 175 µL of aqueous polymer solutions at appropriate concentrations to 175 µL of pDNA (20 ng/µL in water) to achieve desired N/P values (2.5, and 5) as described earlier. The polymer-pDNA mixtures were vortexed and kept at room temperature for an hour before using them for transfections. Transfections were carried out 24 hours after plating. DMEM was aspirated off from each well and cells were washed with 1×PBS. Polyplexes were diluted two times with either reduced-serum OptiMEM or DMEM containing 10% FBS. The diluted solution (300 µL) was then added to each well. Four hours after transfection, 1 mL of DMEM containing 10% FBS was added to each well. Twenty four hours after transfection, culture medium was replaced with fresh DMEM containing 10% FBS. Forty eight hours after transfection, the culture medium was aspirated off and the cells were washed with 1×PBS. The luciferase assay system was purchased from Promega (Madison, Wis.). An aliquot (100 µL) of 1× lysis buffer was added to each well and kept at room temperature for a minimum of 10 minutes to allow cell lysis to occur. Cell lysate (5 µL) was then pipetted into an opaque 96-well plate. After addition of 100 µL of luciferase substrate, the luminescence was measured using a TECAN GENios Pro microplate reader from Tecan (Mannedorf, Switzerland). Protein concentration in each sample was measured using Quick Start Protein Assay Kit from Bio-Rad Laboratories (Hercules, Calif.).

Figure 16:
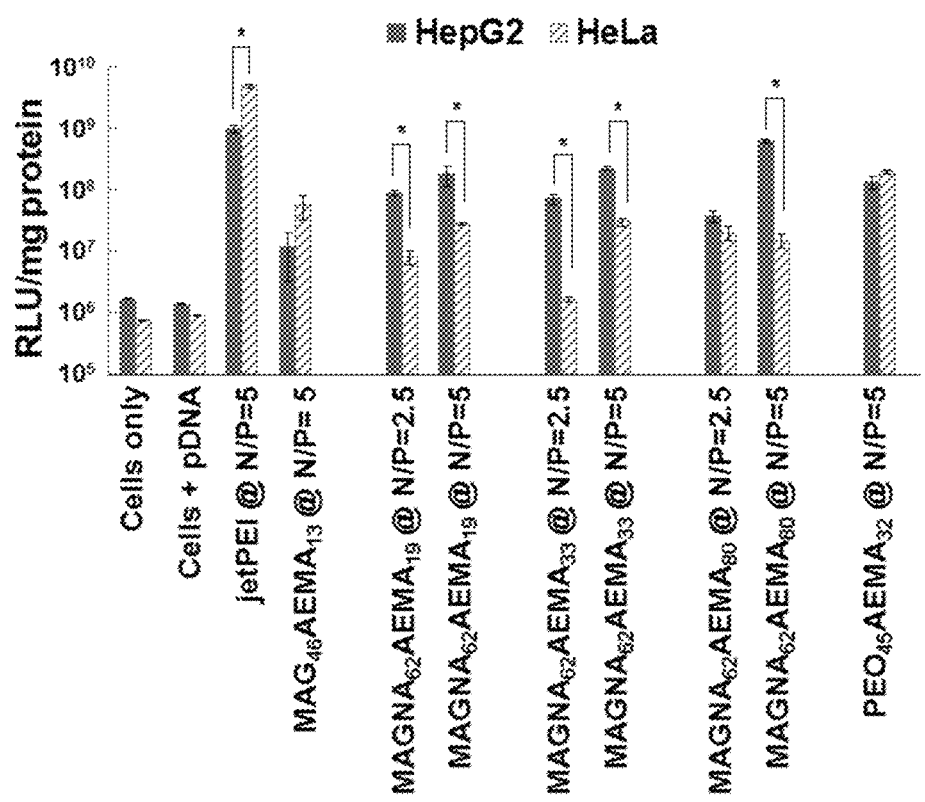
FIG. 16 shows a comparison of luciferase activity in HepG2 (blue, solid bars) and HeLa cells (red, diagonal hashed bars).

FIG. 16 shows a comparison of luciferase activity in HepG2 (blue, solid bars) and HeLa cells (red, diagonal hashed bars). The luciferase assay was performed 48 hours after transfection. The relative light units per mg of protein (RLU/mg protein) is reported as mean±SD (n=3). The asterisks indicate that the measurements were statistically different (p<0.05).

Transfection efficiency was further studied by quantitating luciferase reporter gene expression for each polyplex formulation. HepG2 and HeLa cells were transfected with polyplexes containing gWiz-luc plasmid at N/P values of 2.5 and 5. In accordance with our hypothesis, HepG2 cells exhibited higher luciferase activity than HeLa cells when gWiz-luc was delivered with MAGalNAc-containing block polymers (FIG. 16). HepG2 cells have been found to display approximately 76,000 ASGP receptors on the cell surface that can bind with the ligands in MAGalNAc polyplex formulations. The lack of these receptors in HeLa cells likely leads to lower protein expression. In contrast to MAGalNAc-containing formulations, the controls, $MAG_{46}AEMA_{13}$, $PEO_{45}AEMA_{32}$, and JetPEI formulations show similar or higher gene expression in HeLa compared to HepG2 cells. This demonstrates the role of GNA ligands in promoting internalization of pDNA through specific pathways (ASGP receptors) that promote efficacious delivery. Interestingly, when polyplexes were formulated with a mixture of $MAGalNAc_{62}AEMA_{33}$ and $PEO_{45}AEMA_{32}$, the selectivity towards HepG2 was dose-dependent on $MAGalNAc_{62}AEMA_{33}$, which further validates the role of GNA ligands.

It should be noted that the total MFI value for each MAGalNAc polyplex formulation was similar or higher in HeLa compared to HepG2 cells, suggesting a similar level of binding to both cell types irrespective of the presence of the ASGP cell surface receptors (FIGS. 14A and 14B). This may be due to the net positive charge on polyplexes which may facilitate nonspecific interactions with negatively charged glycosaminoglycans on the cell membrane. However, higher protein expression in HepG2 may suggest that an active uptake by receptor-mediated endocytosis leads to more efficacious pDNA delivery and transgene expression. It is interesting to note that efficient gene delivery is achieved at low N/P ratios (2.5 and 5) compared to previously reported non-targeted glycopolycations. This may suggest that the positive charge or excess free polymer may play a more important role in non-specific cell surface interactions and uptake (non-targeted systems) than the receptor-targeted uptake mechanism promoted by targeting groups.

Addition of up to 10 mM GNA did not have a statistically significant effect on uptake or protein expression (data not shown). Higher concentrations of GNA were not studied as significant toxicity was observed at 10 mM. The decrease in uptake due to inhibition by GNA could not be statistically distinguished from the decrease in cell viability. The lack of significant inhibition of polyplex internalization by GNA at these concentrations is likely due to the increased affinity of multivalent poly(MAGalNAc) ligand-receptor interactions. The effect of ligand valency on binding affinity to ASGP receptors is well documented. Previous studies have shown that biantennary and triantennary structures can have three to four orders of magnitude higher binding affinities to ASGP receptors compared to monovalent structures as indicated by half maximal inhibitory concentrations ($IC_{50}$). The serial arrangement of GNA in a block of 62 units may have a similar effect on binding affinity such that polymer chains at concentrations of 1.5 to 4.5 µM in polyplex formulations cannot be effectively inhibited by 10 mM GNA. An earlier study with glucose, which has very weak affinity for ASGP receptors, showed that such an arrangement can lead to a markedly enhanced cell type-specific uptake. To the best of our knowledge, this work is the first report of using polymerized GNA ligands to achieve high valency of ligand-receptor interaction.

In Vivo Biodistribution Studies

All animal work was carried out in accordance with IACUC guidelines. Animals were housed in the Research Animal Resources facility at the University of Minnesota. For in vivo biodistribution studies, a 40 µg dose of pDNA was delivered with polymers $MAGalNAc_{62}AEMA_{33}$, $MAG_{46}AEMA_{13}$ or in vivo-jetPEI via tail-vein injections in mice. Three mice were injected for each study group, unless otherwise stated. Polyplexes were formulated in 5% dextrose solution. At day 1, mice were given intra-peritoneal injections of 100 µL of 25 mg/mL D-luciferin and imaged with an IVIS Spectrum Pre-clinical In Vivo Imaging System from Perkin Elmer Inc (Waltham, Mass.). Animals were euthanized immediately after and tissues (liver, left lung, heart, left kidney, spleen) and blood were collected. All the samples were flash-frozen in liquid nitrogen, and stored at −80° C. until further processing. DNA was purified from the tissues by phenol-chloroform extraction. The amount of plasmid DNA in each tissue was determined by quantitative polymerase chain reaction (qPCR), which was run at the University of Minnesota Genomics Center. The data are presented as copies of pDNA per genome equivalent of total DNA.

To quantify the amount of polymer in various tissues, $MAGalNAc_{62}AEMA_{33}$ and $MAG_{46}AEMA_{13}$ were labeled with a Cy7 fluorophore using Cy7-NHS ester from Lumiprobe (Hallandale Beach, Fla.). Three mice each were injected with 40 µg of pT2/CAL complexed with the Cy7-labeled polymers at desired N/P values. Mice were euthanized 30 minutes after injections and the tissues (liver, left lung, heart, left kidney, spleen) and blood were harvested. All the samples were stored at −80° C. Tissues were imaged for Cy7 content with the IVIS Spectrum Pre-clinical In Vivo Imaging System from Perkin Elmer Inc (Waltham, Mass.). The background fluorescence was subtracted from each sample. The distribution data for individual tissues are presented as a fraction of total fluorescence in all the harvested samples.

In vivo distribution of pDNA and the MAGalNAc block copolycations was studied by qPCR and fluorescence imaging, respectively. For qPCR studies, a dose of 40 µg pT2/CAL pDNA was formulated with $MAGalNAc_{62}AEMA_{33}$ at N/P=2.5 and N/P=5 and administered to C57BL/6 mice via tail-vein injection. In vivo-jetPEI (N/P=8) and the glucose-derived $MAG_{46}AEMA_{13}$ polymers were used as controls to compare the data for $MAGalNAc_{62}AMEA_{33}$. At day 1 after administration, mice were euthanized for harvesting tissues and DNA was purified from each tissue by phenol-chloroform extraction. The amount of pDNA in each tissue was quantified by quantitative PCR (qPCR) against the luciferase gene (Table 2). A clear difference was observed between the biodistribution of pDNA delivered with $MAGalNAc_{62}AEMA_{33}$ formulated with pDNA at N/P=2.5 and N/P=5. For polyplex formulations at N/P=2.5, the qPCR threshold cycle ($C_T$) value for pDNA in the lungs was lower (p<0.05) than that observed in the liver. Polyplexes formulated with $MAGalNAc_{62}AEMA_{33}$ at N/P=5 or in vivo-jetPEI at N/P=8 did not show a statistically significant difference in $C_T$ values for the lungs or liver. As a non-targeted control, polyplexes formulated with $MAG_{46}AEMA_{13}$ at N/P=5 revealed a lower amount of pDNA (higher $C_T$ value) in the liver compared to other polymers studied. It is interesting to note the low amount of pDNA present all organs with $MAG_{46}AEMA_{13}$, indicating that this vehicle type circulates well in vivo and discourages non-specific organ interactions.

TABLE 2

Quantitative PCR threshold cycle ($C_T$) values for pDNA in various tissues

| | $MAGalNAc_{62}AEMA_{33}$ @ N/P = 2.5 | $MAGalNAc_{62}AEMA_{33}$ @ N/P = 5 | In vivo-jetPEI @ N/P = 8 | $MAG_{46}AEMA_{13}$ @ N/P = 5 |
|---|---|---|---|---|
| Liver | 16.6 ± 2.2 | 15.5 ± 1.0 | 14.8 ± 1.3 | 29.0 ± 1.2 |
| Lung | 23.7 ± 3.8 | 15.5 ± 1.7 | 14.6 ± 1.3 | 25.7 ± 1.4 |
| Heart | 18.9 ± 0.2 | 17.4 ± 0.9 | 17.7 ± 1.2 | 28.3 ± 0.7 |
| Kidney | 25.5 ± 1.9 | 20.8 ± 3.2 | 21.6 ± 1.1 | 27.6 ± 1.1 |
| Spleen | 18.8 ± 1.0 | 17.9 ± 2.7 | 15.6 ± 0.8 | 29.2 ± 0.6 |

Figure 17A:
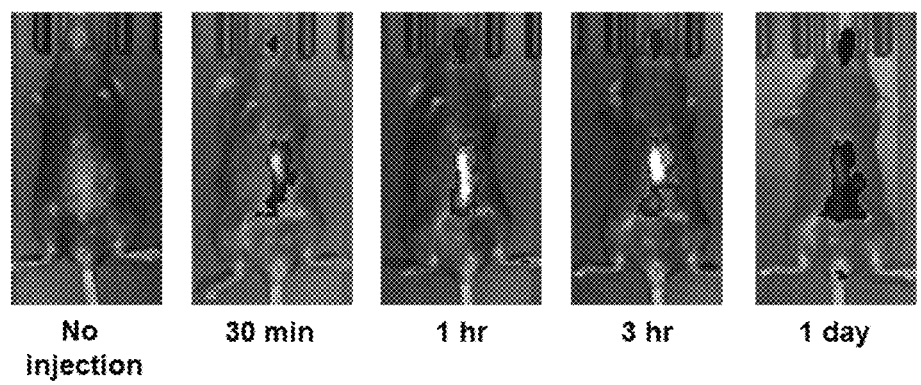
FIGS. 17A and 17B show the time-course imaging of fluorescence in vivo after injection of 40 pDNA complexed with Cy7-labeled $MAGalNAc_{62}AEMA_{33}$ @ N/P=2.5 (FIG. 17A); and the biodistribution of Cy7-labeled $MAGalNAc_{62}AEMA_{33}$ @ N/P=2.5 (blue, solid fill) and N/P=5 (red, diagonal fill), and Cy7-labeled $MAG_{46}AEMA_{13}$ @ N/P=5 (green, dot fill) in various tissues as determined by fluorescence imaging at 30 minutes post administration (FIG. 17B).
Figure 17B:
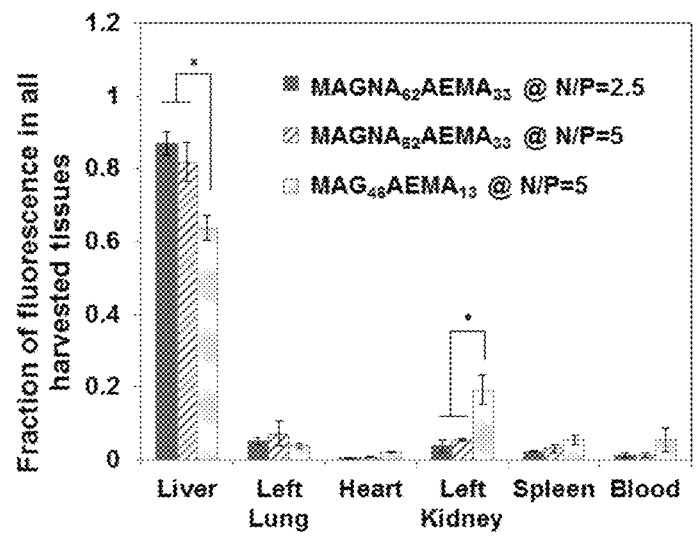

To further understand the biodistribution, $MAGalNAc_{62}AEMA_{33}$ and $MAG_{46}AEMA_{13}$ were labeled with a Cy7 fluorophore, complexed with 40 µg pDNA, and administered to mice via tail-vein injections. FIG. 17A shows the time-course imaging of fluorescence in vivo after injection of 40 µg pDNA complexed with Cy7-labeled $MAGalNAc_{62}AEMA_{33}$ @ N/P=2.5. FIG. 17B shows the biodistribution of Cy7-labeled $MAGalNAc_{62}AEMA_{33}$ @ N/P=2.5 (blue, solid fill) and N/P=5 (red, diagonal fill), and Cy7-labeled $MAG_{46}AEMA_{13}$ @ N/P=5 (green, dot fill) in various tissues as determined by fluorescence imaging at 30 minutes post administration.

The time-course images of fluorescence in whole animal (FIG. 17A) revealed localization of polymer to the liver within 30 minutes post injection. The highest total fluorescence was seen at 1 hr post injection, whereas the image at 30 min showed the smallest area over which the fluorescence was spread. The polyplexes localize to the liver quickly and get cleared over time as suggested by the decreased fluorescence at 3 hr and 1 day post injection. To get a better picture of fluorescence in individual tissues, selected tissues were harvested 30 minutes post-injection and imaged to measure fluorescence in each of them. The data are presented in FIG. 17B as a fraction of total fluorescence in all the harvested tissues from each mouse. No difference in MAGalNAc$_{62}$AEMA$_{33}$ biodistribution was observed when comparing N/P=2.5 and N/P=5 formulations (p>0.05). At both N/P ratios, liver samples contributed to about 80% of the total measured fluorescence from MAGalNAc$_{62}$AEMA$_{33}$ which can be attributed to its large size compared to other organs. MAG$_{46}$AEMA$_{13}$ resulted in a lower amount of polymer in the liver (64% of total fluorescence) when compared to the MAGalNAc$_{62}$AEMA$_{33}$ polyplexes (P<0.01). A higher quantity of MAG$_{46}$AEMA$_{13}$ was present in kidneys (20% of total fluorescence) compared with MAGalNAc$_{62}$AEMA$_{33}$ (p<0.01). Because the MAG block may not interact as strongly with ASGP receptors on the liver, this polymer may clear more quickly from liver to the kidneys. This may also explain the low pDNA uptake observed in qPCR study (Table 1). The higher amount of MAGalNAc$_{62}$AEMA$_{33}$ in liver tissue compared to MAG$_{46}$AEMA$_{13}$ is in agreement with our hypothesis that GNA ligands on the MAGalNAc block facilitate interactions with the ASGP receptor present on liver cells.

Despite the localization of a higher amount of polymer and pDNA to liver compared with MAG$_{46}$AEMA$_{13}$ polyplexes, MAGalNAc$_{62}$AEMA$_{33}$ did not result in a high amount of protein expression. As reported previously, delivery with in vivo-jetPEI lead to protein expression in the lungs, likely due to aggregation in the blood stream leading to accumulation in the pulmonary capillary bed. The lack of protein expression from MAGalNAc$_{62}$AEMA$_{33}$ vehicle could be due to the inability to deliver sufficient amount of pDNA to hepatocytes and/or slow trafficking of pDNA to the nucleus of hepatocytes. The liver is a complex organ composed of various cell types such as hepatocytes, Kupffer cells and endothelial cells. The hepatic sinusoidal epithelium presents a structural barrier with fenestrations of approximately 150 nm size. An increase in polyplex size due to interaction with blood components could prevent access to hepatocytes thereby promoting uptake by Kupffer cells lining the liver sinusoid. Interaction of polyplexes with serum proteins has also been shown to promote clearance by the RES. The high levels of pDNA in both liver and spleen (about 100 copies per genome equivalent) suggest this mechanism of clearance. On the other hand, breakdown of polyplexes may release pDNA leading to uptake by liver endothelial cells and thus localization to the liver.[56] Knowledge of pDNA localization at the cellular level in liver is critical for further improvement in these glycopolymeric delivery systems and currently the subject of future studies.

Receptor-mediated targeting of nanoparticles has proved promising for delivery of siRNA to liver, but few studies have shown in vivo success for pDNA delivery with the exception of hydrodynamic delivery. To achieve protein expression for therapeutic applications, pDNA must be delivered to the nucleus of target cell types in sufficient quantity. In this work, we achieved stable nanoparticles by designing an outer layer composed of MAGalNAc blocks carrying GNA ligands known for high affinity to the ASGP receptors on hepatocytes. In vitro and in vivo studies demonstrated the ability of these polymers to efficiently deliver pDNA to receptor-specific cell types.

Disclosed herein is illustrated the synthesis and polymerization of a novel N-acetylgalactosamine-derived monomer (MAGalNAc) was completed to create a series of diblock glycopolycations. The MAGalNAc block copolymerized with three different lengths of cationic AEMA blocks formed polyplexes that exhibited higher colloidal stability than similar polycations copolymerized from a PEG block. The presence of GNA ligands on the MAGalNAc block promoted cell type-dependent delivery, with higher transgene expression with HepG2 (contains the ASGP receptor) as compared to HeLa (lacks ASGP receptor) cells. In comparison, diblock polycations with hydrophilic PEG or MAG blocks show similar expression profiles in both HepG2 and HeLa cells. In vivo biodistribution experiments in mice revealed a higher amount of pDNA in liver as compared to lungs and other organs when delivered with MAGalNAc$_{62}$AEMA$_{33}$ at N/P=2.5. This difference was not observed at N/P=5 or with MAG$_{46}$AEMA$_{13}$ or in vivo-jetPEI polymers. In addition, Cy7-labeled MAGalNAc$_{62}$AEMA$_{33}$ revealed a higher fraction of polymer localization to the liver compared to the non-targeted MAG$_{46}$AEMA$_{13}$ control. Polymerization of GNA offers a facile and design motif for functionalizing nanosystems for targeted delivery of therapeutics and diagnostic agents to the liver. Indeed, further investigation of the effect of blood components on these polyplexes and their localization at the cellular level within the liver will provide useful insights and guide the future design of efficacious delivery vehicles that promote high gene expression.

Thus, embodiments of polymers including galactose based blocks are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

The invention claimed is:

1. A block copolymer comprising:
   one or more N-acetyl-D-galactosamine (GNA) based blocks; and
   one or more cationic blocks.

2. The block copolymer according to claim 1, wherein the one or more cationic blocks comprise aminoethylmethacrylamide (AEMA), 3-guanidinopropyl methacrylamide (GPMA), or combinations thereof.

3. The block copolymer according to claim 1, wherein the one or more N-acetyl-D-galactosamine (GNA) based block comprises methacrylamido N-acetyl-D-galactosamine (MAGalNAc).

4. The block copolymer according to claim 1, wherein there are at least 10 repeating units of the cationic block.

5. The block copolymer according to claim 1, wherein there are at least 30 repeating units of the cationic block.

6. The block copolymer according to claim 1, wherein there are at least 40 repeating units of the N-acetyl-D-galactosamine (GNA) based block.

7. The block copolymer according to claim 1, wherein there are at least 60 repeating units of the N-acetyl-D-galactosamine (GNA) based block.

8. A polyplex comprising:
   a block copolymer comprising:
      one or more N-acetyl-D-galactosamine (GNA) based blocks; and
      one or more cationic blocks; and
      one or more nucleic acids.

9. The polyplex according to claim 8, wherein the one or more cationic blocks comprise aminoethylmethacrylamide (AEMA), 3-guanidinopropyl methacrylamide (GPMA), or combinations thereof.

10. The polyplex according to claim 8, wherein the one or more N-acetyl-D-galactosamine (GNA) based block comprises methacrylamido N-acetyl-D-galactosamine (MAGalNAc).

11. The polyplex according to claim 8, wherein there are at least 10 repeating units of the cationic block.

12. The polyplex according to claim 8, wherein there are at least 40 repeating units of the N-acetyl-D-galactosamine (GNA) based block.

13. A method of delivering a nucleic acid to a cell, the method comprising:
   delivering a polyplex to a cell, the polyplex comprising:
      a block copolymer comprising:
         one or more N-acetyl-D-galactosamine (GNA) based blocks; and
         one or more cationic blocks; and
      one or more nucleic acids.

14. The method according to claim 13, wherein the one or more cationic blocks comprise aminoethylmethacrylamide (AEMA), 3-guanidinopropyl methacrylamide (GPMA), or combinations thereof.

15. The method according to claim 13, wherein the one or more N-acetyl-D-galactosamine (GNA) based block comprises methacrylamido N-acetyl-D-galactosamine (MAGalNAc).

16. The method according to claim 13, wherein there are at least 10 repeating units of the cationic block.

17. The method according to claim 13, wherein there are at least 40 repeating units of the N-acetyl-D-galactosamine (GNA) based block.

* * * * *